(12) United States Patent
Hadian et al.

(10) Patent No.: US 10,875,856 B2
(45) Date of Patent: Dec. 29, 2020

(54) CPAP-TUBULIN MODULE

(71) Applicants: UNIVERSITAET ZU KOELN, Cologne (DE); HELMHOLTZ ZENTRUM MUENCHEN, Neuherberg (DE)

(72) Inventors: Kamyar Hadian, Munich (DE); Karl Kenji Schorpp, Munich (DE); Michael Sattler, Munich (DE); Komal Soni, Heidelberg-Rohrbach (DE); Jay Gopalakrishnan, Duesseldorf (DE)

(73) Assignees: UNIVERSITAET ZU KOELN, Cologne (DE); HELMHOLTZ ZENTRUM MUENCHEN, Neuherberg (DE)

( * ) Notice: Subject to any disclaimer, the term of this patent is extended or adjusted under 35 U.S.C. 154(b) by 0 days.

(21) Appl. No.: 16/060,425

(22) PCT Filed: Dec. 8, 2016

(86) PCT No.: PCT/EP2016/080316
§ 371 (c)(1),
(2) Date: Jun. 8, 2018

(87) PCT Pub. No.: WO2017/097928
PCT Pub. Date: Jun. 15, 2017

(65) Prior Publication Data
US 2018/0362527 A1  Dec. 20, 2018

(30) Foreign Application Priority Data

Dec. 8, 2015  (EP) .................................... 15198526

(51) Int. Cl.
| | | |
|---|---|---|
| *C07D 471/04* | (2006.01) | |
| *A61K 31/4745* | (2006.01) | |
| *A61K 31/517* | (2006.01) | |
| *A61K 31/55* | (2006.01) | |
| *C07D 495/14* | (2006.01) | |
| *A61P 35/00* | (2006.01) | |
| *A61K 45/06* | (2006.01) | |

(52) U.S. Cl.
CPC ........ *C07D 471/04* (2013.01); *A61K 31/4745* (2013.01); *A61K 31/517* (2013.01); *A61K 31/55* (2013.01); *A61K 45/06* (2013.01); *A61P 35/00* (2018.01); *C07D 495/14* (2013.01)

(58) Field of Classification Search
CPC .. A61K 31/4745; A61K 31/517; A61K 31/55; A61K 45/06; C07D 471/04; C07D 495/14; A61P 35/00
See application file for complete search history.

(56) References Cited

U.S. PATENT DOCUMENTS 6,864,238 B1  3/2005 Tang et al.
2009/0118135 A1  5/2009 Reed et al.

FOREIGN PATENT DOCUMENTS

WO  03097642 A1  11/2003

OTHER PUBLICATIONS

Bhatia et. al., Nature Biotechnology, 2012, Nature Publishing Group, vol. 30(7), pp. 604-610 (Year: 2012).*
Leaf, Fortune, 2004, Time Inc., pp. 1-26 (Year: 2004).*
Kaiser, Science, 2012, AAAS, vol. 337, pp. 282-284 (Year: 2012).*
Wistuba et. al., Nature Rev. Clin. Oncology, 2011, Nature Publishing Group, vol. 8, pp. 135-141 (Year: 2011).*
Singh, European J. Med. Chem., 2014, Elsevier, vol. 74, pp. 440-450 (Year: 2014).*
Moszew et. al., Chemiczne, 1966, Abstract (Year: 1966).*
Bernardino et al: "SAR of a series of anti-HSV-I acridone derivatives and a rational acridone-based design of a new anti-HSV-I 3H-benzo [b] pyrazolo[3,4-h]-1 , 6-naphthyridine series", Bioorganic & Medicinal Chemistry, Jan. 1, 2008 (Jan. 1, 2008) , pp. 313-321.
Chen Q et al: "Electron-Deficient DNA Intercalating Agents as Antitumor Drugs: Aza Analogs of the Experimental Clinical Agent N-[2-(Dimethyl amino)ethyl]acridine4-carboxamide" Journal of Medicinal Chemistry, vol . 37, No. 5, Jan. 1, 1994 (Jan. 1, 1994), pp. 593-597.
Database Caplus [Online] Chemical Abstracts Service, Columbus, Ohio, US; Dec. 22, 2011 (Dec. 22, 2011) , XP002755369 , retrieved from STN Database accession No. 2011: 1619070 the whole document RN 1351579-10-6.
Database Caplus [Online] Chemical Abstracts Service, Columbus, Ohio, US; Dec. 22, 2011 (Dec. 22, 2011), XP002755370, retrieved from STN Database accession No. 2011: 1407166 abstract RN 1351442-37-9.
Deady et al: "Novel derivatives of the benzo [b] [1,6]naphthyridine system" Journal of Heterocyclic Chemistry, vol. 43, no. 2, Mar. 13, 2006 (Mar. 13, 2006), pp. 405-416.
Deady et al: "Synthesis and Cytotoxic Activity of Carboxamide Derivatives of Benzo [ b] [1,6] naphthyridines" Journal of Medicinal Chemistry, vol. 46, No. 6, Mar. 1, 2003 (Mar. 1, 2003), pp. 1049-1054.

(Continued)

*Primary Examiner* — Sarah Pihonak
(74) *Attorney, Agent, or Firm* — Agris & Von Natzmer, LLP; Joyce Von Natzmer

(57) ABSTRACT

The invention relates to CPAP-tubulin inhibitors having the general formula (1) or a physiologically acceptable salt thereof; and their use as cancer therapeutics.

(1)

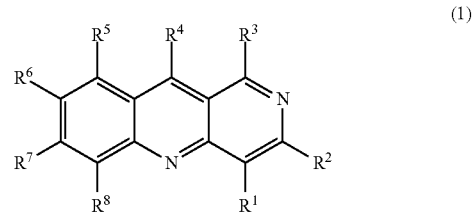

30 Claims, 14 Drawing Sheets

(56) References Cited

OTHER PUBLICATIONS

Deady et al: "Synthesis and cytotoxic activity of carboxamide derivatives of benzo [b] [1,6] naphthyridin-(5H)ones" Bioorganic & Medicinal Chemistry, vol. 13, No. 4, Feb. 15, 2005 (Feb. 15, 2005), pp. 1341-1355.

Khmeli'nistskaya et al: "Electrochemical behavior of benzo [b] [1,6] naphthyridine derivatives" Russian Chemical Bulletin, May 1, 2003 (May 1, 2003), pp. 1157-1160.

Nathan A. Lack et al: "Targeting the Binding Function 3 (BF3) Site of the Human Androgen Receptor through Virtual Screening" Journal of Medicinal Chemistry, vol. 54, No. 24, Dec. 22, 2011 (Dec. 22, 2011), pp. 8563-8573.

Pradeep B Lukka et al: "Comparison of a homologous series of benzonaphthyridine anti-cancer agents in mice: divergence between tumour and plasma pharmacokinetics" Cancer Chemotherapy and Pharmacology, vol. 70, No. 1, Jun. 3, 2012 (Jun. 3, 2012), pp. 151-160.

Rivalle et al: "Nouvelle Synthese Des Pyrido (4,3-B) Quinoleine Substituees Sur Leursommet 1" Journal of Heterocyclic Chemistry, vol. 245, No. 8, Mar. 1, 1980 (Mar. 1, 1980), pp. 245-248.

Tugusheva: "Synthesis and Biological Activity of Monoand Tricyclic Derivatives of 2-Amino-3-Cyanopyridine" Pharmaceutical Chemistry Journal, Jan. 1, 1986 (Jan. 1, 1986), pp. 483-488.

Ivanov et al: "Study of reactions of 3-chloro-4-cyanobenzo [b] [1,6]naphthyridine with nucleophilic reagents," Russian Chemical Bulletin International Edition Seriya Khimicheskaya, Nov. 1, 2002, pp. 2121-2128.

National Intellectual Property Administration, PRC, Office Action for CN 201680071539.3, CPAP-Tubulin Module, Jun. 10, 2020 (Chinese Original and English Translation).

STN Registry, 3-(1-Piperidinyl)benzo[b] [1,6] naphthyridine-4-carbonitrile, CAS: 352554-17-7, Aug. 24, 2001.

STN Registry, 3-(Hexahydro-1H-azepin-1-yl) benzo[b] [1,6] naphthyridine-4-carbonitrile, CAS: 506429-60-3, Apr. 28, 2003.

* cited by examiner

CPAP-TUBULIN MODULE

CROSS-REFERENCE TO RELATED APPLICATIONS

This is the U.S. national stage of International application PCT/EP2016/080316, filed Dec. 8, 2016 designating the United States and claiming priority to European patent application EP 15198526.4, filed Dec. 8, 2015.

The invention relates to CPAP-tubulin inhibitors and their use as cancer therapeutics.

Centrosome amplification is a hallmark of human cancers that can trigger cancer cell invasion. Centrosomes are major microtubule organizing centers in mammalian cells whose numerical abnormalities contribute to increased cellular invasiveness. In contrast to normal fibroblasts with a pair of centrosomes, usually cancer cells display supernumerary centrosomes. In particular, non-small-cell lung cancer cells harboring somatic activating and resistance mutations in epidermal growth factor receptor (EGFR) gene exhibit an extreme increase in centrosome numbers. Cancer cells cluster their supernumerary centrosomes both at interphase and mitosis to generate pseudo-bipolar spindles so as to circumvent the deleterious effects of centrosomal amplification caused by mitotic catastrophe.

While the mechanisms by which cancer cells cluster their supernumerary centrosomes are largely unknown, it is known that extra-centrosomes remain inactive with no or less microtubule nucleating activity both during and after centrosomal clustering at the interphase of cell cycle. Further, it is known that microtubule-nucleating activity of centrosomes is spatiotemporally regulated so that they nucleate less during interphase and more during mitosis. Still further, it is known that in order to combat cancer, centrosomes can be removed. However, cancer cells can proliferate upon centrosome removal, raising the possibility that cancer cells use the extra-centrosomes for the benefit of cellular invasion. In the context of centrosomes, reference can be made, for example, to Blachon and Gopalakrishnan et al., Genetics 2008; Gopalakrishnan et al., JBC 2010; Gopalakrishnan et al., Nature Commun 2011; Gopalakrishnan et al., Nature Cell Biology 2012; Gopalakrishnan et al., Current Opinion in Cell Biol 2013; Zheng et al., PNAS 2014; and Pannu et al., Cell Death and Dis 2014.

Different approaches to combat cancer are known and include inter alia anti-microtubule agents that block cell division by preventing microtubule function. The two main groups of anti-microtubule agents are vinca alkaloids and taxanes. The vinca alkaloids prevent the formation of the microtubules, whereas the taxanes prevent the microtubule disassembly. By doing so, they prevent the cancer cells from completing mitosis. Following this, cell cycle arrest occurs, which induces programmed cell death (apoptosis). Further, topoisomerase inhibitors are employed in cancer therapies. These inhibitors affect the activity of topoisomerase enzymes which unwind DNA during replication or transcription. Another group of compounds for cancer therapy are tyrosine-kinase inhibitors such as compounds kown under the name of Imatinib, Gefitinib, Erlotinib, Sunitinib and Cabozantinib.

The most common medications affect mainly the fast-dividing cells of the body, such as blood cells and the cells lining the mouth, stomach, and intestines. Unfortunately, common drugs used in chemotherapy do not preoperly differentiate between healthy cells and cancer cells. Next to finding a compound that effectively leads to the apoptosis of cancer cells another concern of cancer research are cells that are and/or become resistant to cancer drugs.

US 2009/0118135 discloses an assay for determining compounds that inhibit activity of a Bcl-2-protein, or affect conversion of Bcl-2 from antiapoptotic to a proapoptotic form. Further, US 2009/0118135 relates to a pro-apoptotic modulator of Bcl which can be linked through GX to a cyclic disulfide loop peptide that binds specifically to breast cancer cells.

Lack, N. A., et al., "*Targeting the Binding Function 3 Site of the Human Androgen Receptor through Virtual Screening*", J. Medicinal Chemistry, 2011, vol. 54, p. 8563-8573, relates to inhibitors that target a site on the androgen receptor that is involved into transcriptional activity of the receptor.

Deady, L. W., et al., "*Synthesis and Cytotoxic Activity of Carboxamide Derivatives of Benzo[b][1,6]naphtyridines*", J. Med. Chem., 2003, vol. 46, p. 1049.1054, discloses 4-N-[2-(dimethylamino)ethyl]carboxamides which were tested for growth inhibitory properties against murine P388 leukemia, Lewis lung carcinoma and human Jurkat leukemia cell lines.

Rivalle, C., et al., "*Nouvelle synthèse des pyrido[4,3-b] quinoléines substituées sur leur sommet 1*", J. Heterocyclic Chem., 1980, vol. 17, p. 245-248, relates to pyrido[4,3-b] quinolines which are substituted with different groups and capable of intercalating into DNA and have anti-tumor properties against leukemia.

Jingping, C., et al., "*Electron-Deficient DNA-Intercalating Agents as Antitumor Drugs: Aza Analogues of the Experimental Clinical Agent N-[2-(Dimethylamino)ethyl] acridine-4-carboxamide*", J. Med. Chem. 1994, vo. 37, p. 593-597; discloses that analogues of N-[2-(Dimethylamino) ethyl]acridine-4-carboxamide (DACA) were synthesized and that these compounds showed DNA binding affinities but were generally less potent cytotoxins than DACA. The only azaacridine to show significant in vivo antileukemic activity was benzo[b][1,5]naphtyridine-6-carboxamide.

Deady, L. W., et al., "*Novel Derivatives of the Benzo[b] [1,6]naphtyridine System*", J. Heterocyclic Chem., 2006, vol. 43, p. 405-416, relates to precursors to a new series of potential antitumor carboxamides.

Pradeep, B., et al., "*Comparison of a homologous series of benzonaphthyridine anti-cancer agents in mice: divergence between tumor and plasma pharmacokinetics*", Cancer Chemother. Pharmacol., 2012, vol, 70, p. 151-160, discloses a DNA-binding benzonaphtyridine which has shown curative activity against colon-38 adenocarcinoma after a single dose n mice.

Deady, L. W., et al., "*Synthesis and cytotoxic activity of carboxamide derivatives of benzo[b][1,6]naphtiyridin-5H) ones*", Bioorganic & Medicinal Chemistry, 2005, vol. 13, p. 1341-1355, discloses that potent cytotoxicity against murine P388 leukemia and Lewis lung carcinoma was retained for compounds bearing a remarkably diverse range of 2-substituents.

WO 03/097642 relates to polycyclic carboxamide compounds wiht cytotoxicity, processes for their preparation, pharmaceutical compositions containing them and their use in therapy, particularly in the treatment and/or prophylaxis of cellular proliferative disorders such as cancer.

Tugusheva, N. Z., et al., "*Synthesis and Biological Activity of Mono- and Tricyclic Derivatives of 2-Amino-3-Cyanopyridine*", Pharmaceutical Chemistry Journal, 1. Jan. 1986, p. 483-488, discloses the synthesis of derivatives of 2-Amino-3-Cyanopyridine and their analysis as an antagonist of bradykinin.

Bernardino, A. M. R., et al., "SAR of a series of anti-HSV-1 acridone derivatives, and a rational acridone-based design of a new anti-HSV-1 3H-benzol[b]pyrazolo[3,4-h]-1,6-naphthyridine series", Bioorganic & Medicinal Chemistry, 2008, vol. 16, p. 313-321, asses the structural features and electronic properties of a series of 1-hydroacridone derivatives described as a new class of non-nucleoside inhibitors of Herpes Simplex Virus-1 (HSV-1).

U.S. Pat. No. 6,864,238 relates to polypeptides that comprise approx. 100-amino acid residue region of a centrosomal P4.1-associated protein (CPAP) that possess microtubule-destabilizing activity, polynucleotides encoding such polypeptides, compositions comprising the polypeptides and polynucleotides, and methods of use thereof. The invention is useful for destabilizing microtubules in eukaryotic cells, including but not limited to cancer cells.

There is a demand for compounds that could provide cancer-selective medication against cancer and substantially avoid affecting the functions of healthy cells of the body, in particular the functions of the centrosomes.

Further, there is a demand for compounds that could be employed in the treatment of cancer which is resistant against cancer drugs.

It was an object of the invention to provide compounds that are capable of reducing cellular invasion. It was another object of the invention to provide compounds that are useful in the treatment of diseases and disorders that are associated with cellular invasion, i.e. cancers.

These objects have been achieved by the subject-matter of the patent claims.

Instead of removing the extra-centrosomes, it was surprisingly found that by modifying their behavior, prematurely activation of the extra-centrosomes and nucleation of microtubules is achieved. Such modification is achieved by the CPAP-tubulin inhibitors according to the invention, namely by preventing tubulin, a negative regulator of centrosome activity, from interacting with the centrosomal protein CPAP. Premature activation of extra-centrosomes either by the CPAP-tubulin inhibitors according to the invention or genetic disruption of CPAP-tubulin interaction specifically causes cancer cells to undergo mitotic catastrophe and cell death. Centrosome activation mediated by the CPAP-tubulin inhibitors according to the invention has broad anti-invasive activity against a wide-spectrum of cancers including tyrosine-kinase inhibitor (TKI) resistant EGFR and KRAS mutant cancers. Further, centrosome activation by the CPAP-tubulin inhibitors according to the invention effectively synergizes these cells to EGFR inhibition.

Accordingly, a general vulnerability of cancer cells to extra centrosomal activation has been identified, which can also be combined with other perturbations as a global concept to target various cancer types including drug resistant cancers. The approach according to the invention provides cancer-selective chemotherapy as it specifically targets cancer cells harboring supernumerary centrosome but spares normal cells.

In a first aspect, the invention relates to a compound according to general formula (1)

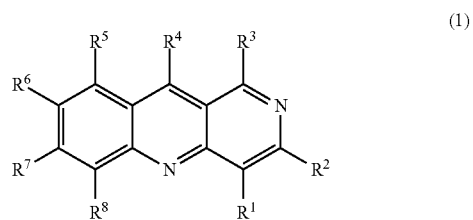

(1)

or a physiologically acceptable salt thereof;
wherein
$R^1$ and $R^2$, independently of one another, represent —F, —Cl, —Br, —I, —CN, —$NO_2$, —CHO, —$R^Z$, —C(=O)$R^Z$, —C(=O)H, —C(=O)OH, —C(=O)O$R^Z$, —C(=O)$NH_2$, —C(=O)NH$R^Z$, —C(=O)N($R^Z$)$_2$, —OH, —O$R^Z$, —OC(=O)H, —OC(=O)$R^Z$, —OC(=O)—O$R^Z$, —OC(=O)NH$R^Z$, —OC(=O)N($R^Z$)$_2$, —SH, —S$R^Z$, —$SO_3$H, —S(=O)$_{1-2}$—$R^Z$, —S(=O)$_{1-2}$$NH_2$, —$NH_2$, —NH$R^Z$, —N($R^Z$)$_2$, —$N^+$($R^Z$)$_3$, —$N^+$($R^Z$)$_2$$O^-$, —NHC(=O)$R^Z$, —NHC(=O)O$R^Z$, —NHC(=O)$NH_2$, —NHC(=O)NH$R^Z$, —NHC(=O)—N($R^Z$)$_2$, —Si($R^Z$)$_3$ or —PO(O$R^Z$)$_2$;
or
$R^1$ and $R^2$ jointly form a five- or six-membered ring, the ring atoms of which respectively independently of one another are C, N, S or O, wherein the ring is aromatic or non-aromatic, unsubstituted or mono- or polysubstituted by substituents selected independently of one another from the group comprising —F, —Cl, —Br, —I, —CN, —$NO_2$, —CHO, —$R^Z$, —C(=O)$R^Z$, —C(=O)H, —C(=O)OH, —C(=O)O$R^Z$, —C(=O)$NH_2$, —C(=O)NH$R^Z$, —C(=O)N($R^Z$)$_2$, —OH, —O$R^Z$, —OC(=O)H, —OC(=O)$R^Z$, —OC(=O)—O$R^Z$, —OC(=O)NH$R^Z$, —OC(=O)N($R^Z$)$_2$, —SH, —S$R^Z$, —$SO_3$H, —S(=O)$_{1-2}$—$R^Z$, —S(=O)$_{1-2}$$NH_2$, —$NH_2$, —NH$R^Z$, —N($R^Z$)$_2$, —$N^+$($R^Z$)$_3$, —$N^+$($R^Z$)$_2$$O^-$, —NHC(=O)$R^Z$, —NHC(=O)O$R^Z$, —NHC(=O) $NH_2$, 细 NHC(=O)NH$R^Z$, —NHC(=O)—N($R^Z$)$_2$, —Si($R^Z$)$_3$ or —PO(O$R^Z$)$_2$;
$R^3$ represents —H, —F, —Cl, —Br, —I, —CN, —$NO_2$, —CHO, —$R^Z$, —C(=O)$R^Z$, —C(=O)H, —C(=O)OH, —C(=O)O$R^Z$, —C(=O)$NH_2$, —C(=O)NH$R^Z$, —C(=O)N($R^Z$)$_2$, —O$R^Z$, —OC(=O)H, —OC(=O)$R^Z$, —OC(=O)—O$R^Z$, —OC(=O)NH$R^Z$, —OC(=O)N($R^Z$)$_2$, —SH, —S$R^Z$, —$SO_3$H, —S(=O)$_{1-2}$—$R^Z$, —S(=O)$_{1-2}$$NH_2$, —$NH_2$, —NH$R^Z$, —N($R^Z$)$_2$, —$N^+$($R^Z$)$_3$, —$N^+$($R^Z$)$_2$$O^-$, —NHC(=O)$R^Z$, —NHC(=O)O$R^Z$, —NHC(=O)$NH_2$, —NHC(=O)NH$R^Z$, —NHC(=O)—N($R^Z$)$_2$, —Si($R^Z$)3 or —PO(O$R^Z$)$_2$;
$R^4$ represents —H, —F, —Cl, —Br, —I, —CN, —$NO_2$, —CHO, —$R^Z$, —C(=O)$R^Z$, —C(=O)H, —C(=O)OH, —C(=O)O$R^Z$, —C(=O)$NH_2$, —C(=O)NH$R^Z$, —C(=O)N($R^Z$)$_2$, —OH, -O$R^Z$, —OC(=O)H, —OC(=O)$R^Z$, —OC(=O)—O$R^Z$, —OC(=O)NH$R^Z$, —OC(=O)N($R^Z$)$_2$, —SH, —S$R^Z$, —$SO_3$H, —S(=O)$_{1-2}$—$R^Z$, —S(=O)$_{1-2}$$NH_2$, —$NH_2$, —NH$R^Z$, —N($R^Z$)$_2$, —$N^+$($R^Z$)$_3$, —$N^+$($R^Z$)$_2$$O^-$, —NHC(=O)$R^Z$, —NHC(=O)O$R^Z$, —NHC(=O)$NH_2$, —NHC(=O) NH$R^Z$, —NHC(=O)—N($R^Z$)$_2$, —Si($R^Z$)3 or —PO(O$R^Z$)$_2$;
$R^5$ represents —H, —F, —Cl, —Br, —I, —CN, —$NO_2$, —CHO, —$R^Z$, —C(=O)$R^Z$, —C(=O)H, —C(=O)OH, —C(=O)O$R^Z$, —C(=O)$NH_2$, —C(=O)NH$R^Z$, —C(=O)N($R^Z$)$_2$, —OH, —O$R^Z$, —OC(=O)H, —OC(=O)$R^Z$, —OC(=O)—O$R^Z$, —OC(=O)NH$R^Z$, —OC(=O)N(R$^Z$)$_2$, —SH, —SR$^Z$, —SO$_3$H, —S(=O)$_{1-2}$—R$^Z$, —S(=O)$_{1-2}$NH$_2$, —NH$_2$, —NHR$^Z$, —N(R$^Z$)$_2$, —N$^+$(R$^Z$)$_3$, —N$^+$(R$^Z$)$_2$O$^-$, —NHC(=O)R$^Z$, —NHC(=O)OR$^Z$, —NHC(=O)NH$_2$, —NHC(=O)NHR$^Z$, —NHC(=O)—N(R$^Z$)$_2$, —Si(R$^Z$)$_3$ or —PO(OR$^Z$)$_2$;

R$^6$ represents —H, —F, —Cl, —Br, —I, —CN, —NO$_2$, —CHO, —R$^Z$, —C(=O)R$^Z$, —C(=O)H, —C(=O)OH, —C(=O)OR$^Z$, —C(=O)NH$_2$, —C(=O)NHR$^Z$, —C(=O)N(R$^Z$)$_2$, —OH, —OR$^Z$, —OC(=O)H, —OC(=O)R$^Z$, —OC(=O)—OR$^Z$, —OC(=O)NHR$^Z$, —OC(=O)N(R$^Z$)$_2$, —SH, —SR$^Z$, —SO$_3$H, —S(=O)$_{1-2}$—R$^Z$, —S(=O)$_{1-2}$NH$_2$, —NH$_2$, —NHR$^Z$, —N(R$^Z$)$_2$, —N$^+$(R$^Z$)$_3$, —N$^+$(R$^Z$)$_2$O$^-$, —NHC(=O)R$^Z$, —NHC(=O)OR$^Z$, —NHC(=O)NH$_2$, —NHC(=O)NHR$^Z$, —NHC(=O)—N(R$^Z$)$_2$, —Si(R$^Z$)$_3$ or —PO(OR$^Z$)$_2$;

R$^7$ represents —H, —F, —Cl, —Br, —I, —CN, —NO$_2$, —CHO, —R$^Z$, —C(=O)R$^Z$, —C(=O)H, —C(=O)OH, —C(=O)OR$^Z$, —C(=O)NH$_2$, —C(=O)NHR$^Z$, —C(=O)N(R$^Z$)$_2$, —OH, —OR$^Z$, —OC(=O)H, —OC(=O)R$^Z$, —OC(=O)—OR$^Z$, —OC(=O)NHR$^Z$, —OC(=O)N(R$^Z$)$_2$, —SH, —SR$^Z$, —SO$_3$H, —S(=O)$_{1-2}$—R$^Z$, —S(=O)$_{1-2}$NH$_2$, —NH$_2$, —NHR$^Z$, —N(R$^Z$)$_2$, —N$^+$(R$^Z$)$_3$, —N$^+$(R$^Z$)$_2$O$^-$, —NHC(=O)R$^Z$, —NHC(=O)OR$^Z$, —NHC(=O)NH$_2$, —NHC(=O)NHR$^Z$, —NHC(=O)—N(R$^Z$)$_2$, —Si(R$^Z$)$_3$ or —PO(OR$^Z$)$_2$;

R$^8$ represents —H, —F, —Cl, —Br, —I, —CN, —NO$_2$, —CHO, —R$^Z$, —C(=O)R$^Z$, —C(=O)H, —C(=O)OH, —C(=O)OR$^Z$, —C(=O)NH$_2$, —C(=O)NHR$^Z$, —C(=O)N(R$^Z$)$_2$, —OH, —OR$^Z$, —OC(=O)H, —OC(=O)R$^Z$, —OC(=O)—OR$^Z$, —OC(=O)NHR$^Z$, —OC(=O)N(R$^Z$)$_2$, —SH, —SR$^Z$, —SO$_3$H, —S(=O)$_{1-2}$—R$^Z$, —S(=O)$_{1-2}$NH$_2$, —NH$_2$, —NHR$^Z$, —N(R$^Z$)$_2$, —N$^+$(R$^Z$)$_3$, —N$^+$(R$^Z$)$_2$O$^-$, —NHC(=O)R$^Z$, —NHC(=O)OR$^Z$, —NHC(=O)NH$_2$, —NHC(=O)NHR$^Z$, —NHC(=O)—N(R$^Z$)$_2$, —Si(R$^Z$)$_3$ or —PO(OR$^Z$)$_2$;

wherein in each case R$^Z$, respectively independently, means —C$_{1-8}$-aliphatic, —C$_{3-12}$-cycloaliphatic, -aryl, -heteroaryl, —C$_{1-8}$-aliphatic-C$_{3-12}$-cycloaliphatic, —C$_{1-8}$-aliphatic-aryl, —C$_{1-8}$-aliphatic-heteroaryl, -C$_{3-8}$-cycloaliphatic-C$_{1-8}$-aliphatic, —C$_{3-8}$-cycloaliphatic-aryl or —C$_{3-8}$-cycloaliphatic-heteroaryl;

wherein in each case "aliphatic", respectively independently, means a branched or unbranched, saturated or a mono- or polyunsaturated, unsubstituted or mono- or polysubstituted, aliphatic hydrocarbon residue;

wherein in each case "cycloaliphatic", respectively independently, means a saturated or a mono- or polyunsaturated, unsubstituted or mono- or polysubstituted, alicyclic, mono- or multicyclic hydrocarbon residue;

wherein in each case with respect to "aliphatic" and "cycloaliphatic", "mono- or polysubstituted", respectively independently, means the mono- or polysubstitution of one or more hydrogen atoms by —F, —Cl, —Br, —I, —CN, —NO$_2$, —CHO, =O, —R$^Z$, —C(=O)R$^Z$, —C(=O)H, —C(=O)OH, —C(=O)OR$^Z$, —C(=O)NH$_2$, —C(=O)NHR$^Z$, —C(=O)N(R$^Z$)$_2$, —OH, —OR$^Z$, —OC(=O)H, —OC(=O)R$^Z$, —OC(=O)—OR$^Z$, —OC(=O)NHR$^Z$, —OC(=O)N(R$^Z$)$_2$, —SH, —SR$^Z$, —SO$_3$H, —S(=O)$_{1-2}$—R$^Z$, —S(=O)$_{1-2}$NH$_2$, —NH$_2$, —NHR$^Z$, —N(R$^Z$)$_2$, —N$^+$(R$^Z$)$_3$, —N$^+$(R$^Z$)$_2$O$^-$, —NHC(=O)R$^Z$, —NHC(=O)OR$^Z$, —NHC(=O)NH$_2$, —NHC(=O)NHR$^Z$, —NHC(=O)—N(R$^Z$)$_2$, —Si(R$^Z$)$_3$ or —PO(OR$^Z$)$_2$;

wherein in each case "aryl", respectively independently, means a carbocyclic ring system with at least one aromatic ring, but without heteroatoms in this ring, wherein, if necessary, the aryl residues can be condensed with further saturated, (partially) unsaturated or aromatic ring systems, and each aryl residue can be present in unsubstituted or mono- or polysubstituted form, wherein the aryl substituents can be the same or different and in any desired and possible position of the aryl;

wherein in each case "heteroaryl", respectively independently, means a 5-, 6- or 7-membered cyclic aromatic residue, which contains 1, 2, 3, 4 or 5 heteroatoms, wherein the heteroatoms, the same or different, are nitrogen, oxygen or sulphur, and the heterocycle can be unsubstituted or mono- or polysubstituted; wherein in the case of the substitution on the heterocycle the substituents can be the same or different and can be in any desired and possible position of the heteroaryl; and wherein the heterocycle can also be part of a bi- or polycyclic system;

wherein in each case with respect to "aryl" and "heteroaryl", "mono- or polysubstituted", respectively independently, means the mono- or polysubstitution of one or more hydrogen atoms of the ring system by substituents selected from the group comprising —F, —Cl, —Br, —I, —CN, —NO$_2$, —CHO, =O, —R$^Z$, —C(=O)R$^Z$, —C(=O)H, —C(=O)OH, —C(=O)OR$^Z$, —C(=O)NH$_2$, —C(=O)NHR$^Z$, —C(=O)—N(R$^Z$)$_2$, —OH, —O(CH$_2$)$_{1-2}$O—, —OR$^Z$, —OC(=O)H, —OC(=O)R$^Z$, —OC(=O)OR$^Z$, —OC(=O)NHR$^Z$, —OC(=O)N(R$^Z$)$_2$, —SH, —SR$^Z$, —SO$_3$H, —S(=O)$_{1-2}$—R$^Z$, —S(=O)$_{1-2}$NH$_2$, —NH$_2$, —NHR$^Z$, —N(R$^Z$)$_2$, —N$^+$(R$^Z$)$_3$, —N$^+$(R$^Z$)$_2$O$^-$, —NHC(=O)R$^Z$, —NHC(=O)OR$^Z$, —NH—C(=O)NH$_2$, —NHC(=O)NHR$^Z$, —NHC(=O)—N(R$^Z$)$_2$, —Si(R$^Z$)$_3$ and —PO(OR$^Z$)$_2$; wherein if necessary N-ring atoms present can be respectively oxidized;

for use in the treatment of cancer, preferably of tyrosine-kinase inhibitor (TKI) resistant EGFR cancer, or KRAS mutant cancer, or drug resistant cancer.

Preferably, the compound according to general formula (1) is for use in the treatment of cancer selected from the group consisting of lung cancer, brain cancer, eye cancer, oral cancer, throat cancer, tongue cancer, trachea cancer, stomach cancer, liver cancer, kidney cancer, pancreatic cancer, gallbladder cancer, colorectal cancer, cancer of the urinary tract, bladder cancer, testicular cancer, ovarian cancer, cervical cancer, endometrial cancer, pancreatic cancer, skin cancer, Hodgkin's lymphoma, non-Hodgkin's lymphoma, breast cancer, and prostate cancer.

More preferably, the compound according to general formula (1) is used in the treatment of lung cancer, most preferred in the treatment of non-small cell lung cancer (NSCLC).

Preferably, R$^1$ represents —CN.

In a preferred embodiment of the compound according to general formula (1), R$^2$ represents —OR$^Z$ or —SR$^Z$.

In another preferred embodiment the compound according to general formula (1), R$^2$ represents —NHR$^Z$ or —NR$^A$R$^B$, wherein R$^A$ and R$^B$ together with the nitrogen atom to which they are attached form a ring and mean —(CH$_2$)$_{2-6}$. Preferably, R$^A$ and R$^B$ together with the nitrogen atom to which they are attached form a ring and mean —(CH$_2$)$_{2-6}$, wherein the ring is aromatic or non-aromatic, unsubstituted or mono- or polysubstituted.

In yet another preferred embodiment, $R^2$ represents —F, —Cl, —Br, or —I.

In a preferred embodiment of the compound according to general formula (1)

$R^1$ and $R^2$, independently of one another, represent —F, —Cl, —Br, —I, —CN, —NO$_2$, —CHO, —O—C$_{1-8}$-aliphatic, —S-aryl, —S—C$_{1-8}$-aliphatic-C(=O)NH-aryl, —NH—C$_{1-8}$-aliphatic, —NH—C$_{1-8}$-aliphatic-aryl or —C$_{3-12}$-cycloaliphatic;

or $R^1$ and $R^2$ jointly form a five- or six-membered ring, the ring atoms of which respectively independently of one another are C, N, S or O, wherein the ring is aromatic or non-aromatic, unsubstituted or mono- or polysubstituted by substituents selected independently of one another from the group comprising —C(=O)O—C$_{1-8}$-aliphatic, —C(=O)—C$_{1-8}$-aliphatic-NH-aryl, —NH$_2$, —NH—C$_{1-8}$-aliphatic or —N(—C$_{1-8}$-aliphatic)$_2$.

In another preferred embodiment of the compound according to general formula (1), $R^1$ represents —F, —Cl, —Br, —I, —CN, —NO$_2$ or —CHO;

$R^2$ represents —F, —Cl, —Br, —I, —CN, —NO$_2$, —CHO, —O—C$_{1-8}$-aliphatic, —S-aryl, —S—C$_{1-8}$-aliphatic-C(=O)NH-aryl, —NH—C$_{1-8}$-aliphatic, —NH—C$_{1-8}$-aliphatic-aryl or —C$_{3-12}$-cycloaliphatic;

or $R^1$ and $R^2$ jointly form a five- or six-membered ring, the ring atoms of which respectively independently of one another are C, N, S or O, wherein the ring is aromatic or non-aromatic, unsubstituted or mono- or polysubstituted by substituents selected independently of one another from the group comprising —C(=O)O—C$_{1-8}$-aliphatic, —C(=O)—C$_{1-8}$-aliphatic-NH-aryl, —NH$_2$, —NH—C$_{1-8}$-aliphatic or —N(—C$_{1-8}$-aliphatic)$_2$.

In a further preferred embodiment according to general formula (1), $R^1$ represents —CN;

$R^2$ represents —F, —Cl, —Br, —I, —O—C$_{1-8}$-alkyl, —S-phenyl, —S—C$_{1-8}$-alkyl-C(=O)NH-phenyl, —NH—C$_{1-8}$-alkyl, —NH—C$_{1-8}$-alkyl-CO$_2$H, —NH—C$_{1-8}$-alkyl-phenyl, or —C$_{3-12}$-cycloalkyl;

or $R^1$ and $R^2$ jointly form a five-membered ring, the ring atoms of which respectively independently of one another are C, N or S, wherein the ring is aromatic, mono- or polysubstituted by substituents selected independently of one another from the group comprising —C(=O)O—C$_{1-8}$-alkyl, —C(=O)—C$_{1-8}$-aliphatic-NH-phenyl or —NH$_2$.

In a further preferred embodiment according to general formula (1), $R^3$, $R^4$, $R^5$, $R^6$, $R^7$ and $R^8$, independently of one another, represent —H, —F, —Cl, —Br, —I, —CN, —NO$_2$, —CHO, —O—C$_{1-8}$-aliphatic, —S-aryl, —S—C$_{1-8}$-aliphatic-C(=O)NH-aryl, —NH—C$_{1-8}$-aliphatic, —NH—C$_{1-8}$-aliphatic-aryl or —C$_{3-12}$-cycloaliphatic.

In a further preferred embodiment according to general formula (1), $R^3$, $R^4$, $R^5$, $R^6$, $R^7$ and $R^8$ represent —H.

Particularly preferred embodiments of the compound according to general formula (1) have the general formula (2)

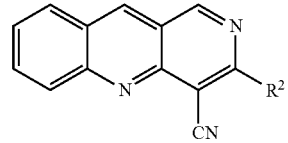

(2)

wherein $R^2$ represents —F, —Cl, —Br, —I, —O—C$_{1-8}$-alkyl, —S-phenyl, —S—C$_{1-8}$-alkyl-C(=O)NH-phenyl, —NH—C$_{1-8}$-alkyl, —NH—C$_{1-8}$-alkyl-phenyl or —C$_{3-12}$-cycloalkyl;

or have the general formula (3)

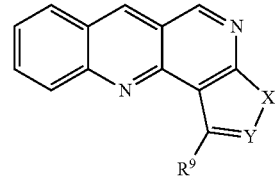

(3)

wherein

X represents —N(H)—, —N(C$_{1-8}$-alkyl)- or —S—;
Y represents N or —C—R$^{10}$;
$R^9$ and $R^{10}$, independently of one another, represent —C(=O)O—C$_{1-8}$-alkyl, —C(=O)—CH$_2$—NH-phenyl or —NH$_2$.

Further particularly preferred embodiments of the compound according to general formula (1) have the general formula (2)

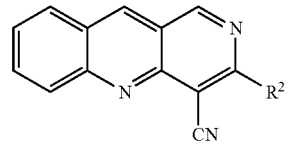

(2)

wherein $R^2$ represents —F, —Cl, —Br, —I, —O—C$_{1-8}$-alkyl, —S-phenyl, —S—C$_{1-8}$-alkyl-C(=O)NH-phenyl, —NH—C$_{1-8}$-alkyl, —NH—C$_{1-8}$-alkyl-CO$_2$H, —NH—C$_{1-8}$-alkyl-phenyl or —C$_{3-12}$-cycloalkyl;

or have the general formula (4)

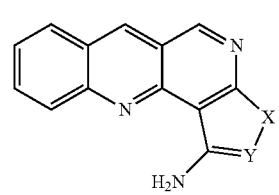

(4)

wherein

X represents —N(H)— or —S—;
Y represents N or —C—R$^{10}$;
$R^{10}$ represent —C(=O)O—C$_{1-8}$-alkyl, —C(=O)—CH$_2$—NH-phenyl or —NH$_2$.

Further particularly preferred embodiments of the compound according to general formula (1) have the general formula (2)

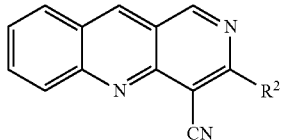

wherein
R² represents —Cl, —O—C₁₋₈-alkyl, —S-phenyl, —S—C₁₋₈-alkyl-C(=O)NH-phenyl, —NH—C₁₋₈-alkyl, —NH—C₁₋₈-alkyl-CO₂H, —NH—C₁₋₈-alkyl-phenyl or —C₃₋₁₂-cycloalkyl;
or have the general formula (4)

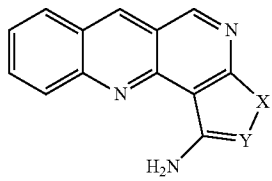

wherein
X represents —N(H)— or —S—;
Y represents N or —C—R¹⁰;
R¹⁰ represent —C(=O)O—C₁₋₈-alkyl or —C(=O)—CH₂—NH-phenyl.

Very particularly preferred embodiments of the compound according to general formula (1) have the general formula (2)

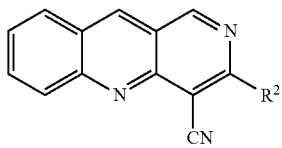

wherein
R² represents —NH—C₁₋₈-alkyl or —NH—C₁₋₈-alkyl-CO₂H, wherein —C₁₋₈-alkyl is unsubstituted.

Further very particularly preferred embodiments of the compound according to general formula (1) have the general formula (2)

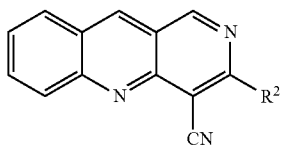

wherein
R² represents —O—C₁₋₈-alkyl or —NH—C₁₋₈-alkyl-CO₂H, wherein —C₁₋₈-alkyl is unsubstituted.

Yet other preferred embodiments of the compound according to general formula (1) have the general formula (3A)

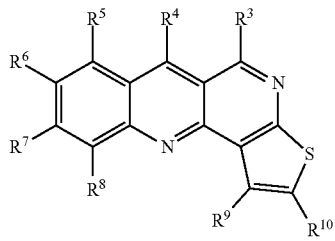

wherein
R⁹ represents —NH₂
and R¹⁰ represents —C(=O)O—C₁₋₈-alkyl or —C(=O)—CH₂—NH-phenyl.

Compounds according to general formula (1) from the following group are most particularly preferred:

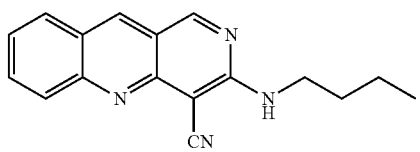

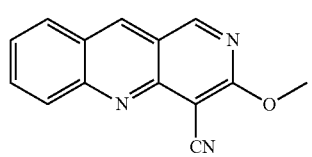

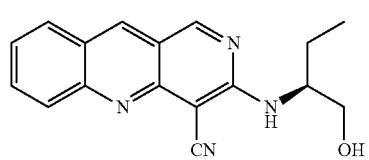

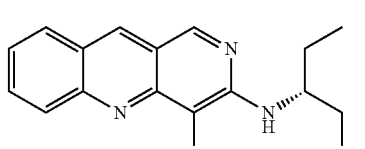

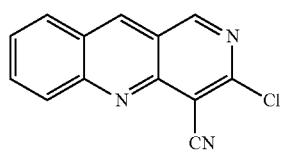

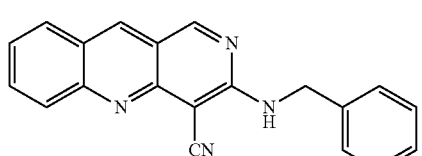

-continued

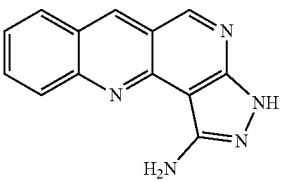
(F)

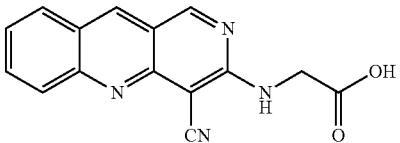
(M)

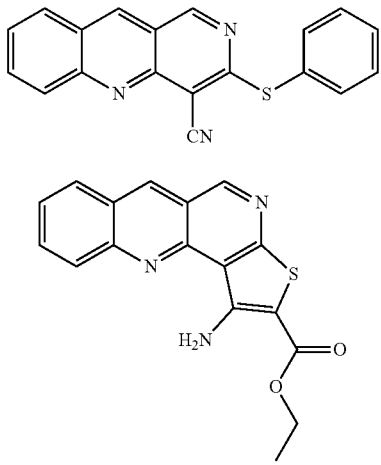
(G)

(H)

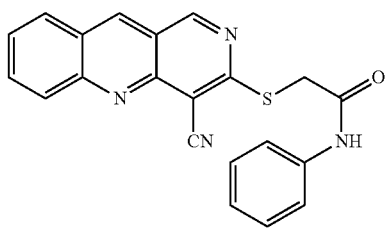
(I)

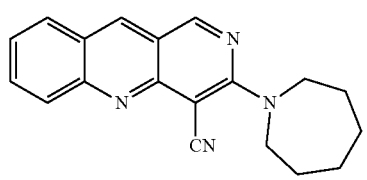
(J)

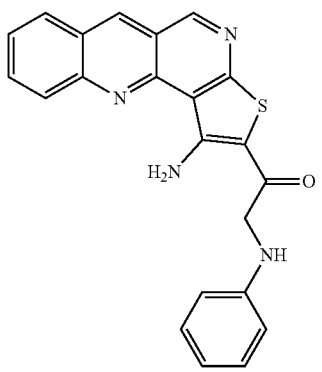
(K)

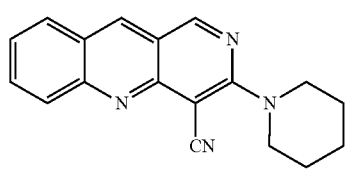
(L)

or a physiologically acceptable salt thereof.

For the purpose of the specification, in the definitions of the compounds according to general formula (1), in each case $R^Z$, respectively independently, means —$C_{1-8}$-aliphatic, —$C_{3-12}$-cycloaliphatic, -aryl, heteroaryl, —$C_{1-8}$-aliphatic-$C_{3-12}$-cycloaliphatic, —$C_{1-8}$-aliphatic-aryl, —$C_{1-8}$-aliphatic-heteroaryl, —$C_{3-8}$-cycloaliphatic-$C_{1-8}$-aliphatic, —$C_{3-8}$-cycloaliphatic-aryl or —$C_{3-8}$-cycloaliphatic-heteroaryl;

in each case "aliphatic", respectively independently, means a branched or unbranched, saturated or a mono- or polyunsaturated, unsubstituted or mono- or polysubstituted, aliphatic hydrocarbon residue;

in each case "cycloaliphatic", respectively independently, means a saturated or a mono- or polyunsaturated, unsubstituted or mono- or polysubstituted, alicyclic, mono- or multicyclic hydrocarbon residue;

in each case with respect to "aliphatic" and "cycloaliphatic", "mono- or polysubstituted", respectively independently, means the mono- or polysubstitution of one or more hydrogen atoms by —F, —Cl, —Br, —I, —CN, —$NO_2$, —CHO, =O, —$R^Z$, —C(=O)$R^Z$, —C(=O)H, —C(=O)OH, —C(=O)O$R^Z$, —C(=O)$NH_2$, —C(=O)NH$R^Z$, —C(=O)N($R^Z$)$_2$, —OH, —O$R^Z$, —OC(=O)H, —OC(=O)$R^Z$, —OC(=O)—O$R^Z$, —OC(=O)NH$R^Z$, —OC(=O)N($R^Z$)$_2$, —SH, —S$R^Z$, —$SO_3H$, —S(=O)$_{1-2}$—$R^Z$, —S(=O)$_{1-2}$$NH_2$, —$NH_2$, —NH$R^Z$, —N($R^Z$)$_2$, —$N^+$($R^Z$)$_3$, —$N^+$($R^Z$)$_2$$O^-$, —NHC(=O)$R^Z$, —NHC(=O)O$R^Z$, —NHC(=O)$NH_2$, —NHC(=O)NH$R^Z$, —NHC(=O)—N($R^Z$)$_2$, —Si($R^Z$)$_3$ or —PO(O$R^Z$)$_2$;

in each case "aryl", respectively independently, means a carbocyclic ring system with at least one aromatic ring, but without heteroatoms in this ring, wherein, if necessary, the aryl residues can be condensed with further saturated, (partially) unsaturated or aromatic ring systems, and each aryl residue can be present in unsubstituted or mono- or polysubstituted form, wherein the aryl substituents can be the same or different and in any desired and possible position of the aryl;

in each case "heteroaryl", respectively independently, means a 5-, 6- or 7-membered cyclic aromatic residue, which contains 1, 2, 3, 4 or 5 heteroatoms, wherein the heteroatoms, the same or different, are nitrogen, oxygen or sulphur, and the heterocycle can be unsubstituted or mono- or polysubstituted; wherein in the case of the substitution on the heterocycle the substituents can be the same or different and can be in any desired and possible position of the heteroaryl; and wherein the heterocycle can also be part of a bi- or polycyclic system;

in each case with respect to "aryl" and "heteroaryl", "mono- or polysubstituted", respectively independently, means the mono- or polysubstitution of one or more hydrogen atoms of the ring system by substituents selected from the group comprising —F, —Cl, —Br, —I, —CN, —$NO_2$, —CHO, =O, —$R^Z$, —C(=O)$R^Z$, —C(=O)H, —C(=O)OH, —C(=O)O$R^Z$, —C(=O)$NH_2$, —C(=O)NH$R^Z$, —C(=O)—N(R$^Z$)$_2$, —OH, —O(CH$_2$)$_{1-2}$O—, —OR$^Z$, —OC(=O)H, —OC(=O)R$^Z$, —OC(=O)OR$^Z$, —OC(=O)NHR$^Z$, —OC(=O)N(R$^Z$)$_2$, —SH, —SR$^Z$, —SO$_3$H, —S(=O)$_{1-2}$—R$^Z$, —S(=O)$_{1-2}$NH$_2$, —NH$_2$, —NHR$^Z$, —N(R$^Z$)$_2$, —N$^+$(R$^Z$)$_3$, —N$^+$(R$^Z$)$_2$O$^-$, —NHC(=O)R$^Z$, —NHC(=O)OR$^Z$, —NH—C(=O)NH$_2$, —NHC(=O)NHR$^Z$, —NHC(=O)—N(R$^Z$)$_2$, —Si(R$^Z$)$_3$ and —PO(OR$^Z$)$_2$; wherein if necessary N-ring atoms present can be respectively oxidized.

In the combination of different residues, e.g. R$^1$, R$^2$ and R$^3$, and also the combination of residues at substituents thereof such as e.g. —OR$^Z$, —SR$^Z$, —S(=O)$_{1-2}$—R$^Z$ or —C(=O)OR$^Z$, a substituent, e.g. R$^Z$, can assume different meanings within a substance for two or more residues, e.g. R$^1$, R$^2$ and R$^3$.

For the purposes of the description hydrocarbon residues are divided into aliphatic hydrocarbon residues and aromatic hydrocarbon residues.

Aliphatic hydrocarbon residues are themselves divided into non-cyclic aliphatic hydrocarbon residues (="aliphatic") and cyclic aliphatic hydrocarbon residues, i.e. alicyclic hydrocarbon residues (="cycloaliphatic"). Cycloaliphatic compounds can be monocyclic or multicyclic. Alicyclic hydrocarbon residues ("cycloaliphatic") comprise both pure aliphatic carbocycles and aliphatic heterocycles, i.e.—unless expressly specified—"cycloaliphatic" comprises pure aliphatic carbocycles (e.g. cyclohexyl), pure aliphatic heterocycles (e.g. piperidyl or piperazyl) and also non-aromatic, multicyclic, possibly mixed, systems (e.g. decalinyl, decahydroquinolinyl).

Aromatic hydrocarbons are themselves divided into carbocyclic aromatic hydrocarbons (="aryl") and heterocyclic aromatic hydrocarbons (="heteroaryl").

The classification of multicyclic, at least partially aromatic systems preferably depends on whether at least one aromatic ring of the multicyclic system has at least one heteroatom (usually N, O or S) in the ring. If at least one such heteroatom is present in this ring, this is preferably a "heteroaryl" (even if a further carbocyclic aromatic or non-aromatic ring with or without heteroatom is possibly present as additionally present cycle of the multicyclic system); if such a heteroatom is not present in any of the possibly several aromatic rings of the multicyclic system, then this is preferably "aryl" (even if a ring heteroatom is present in a possibly additionally present non-aromatic cycle of the multicyclic system).

Therefore, the following priority in the classification applies within the cyclic substituents: heteroaryl>aryl>cycloaliphatic.

For the purposes of the description monovalent and multivalent, i.e. bivalent, hydrocarbon residues are not distinguished between conceptually, i.e. depending on the context, "C$_{1-8}$-aliphatic" covers e.g. —C$_{1-8}$-alkyl, —C$_{1-8}$-alkenyl and —C$_{1-8}$-alkinyl, as well as e.g. —C$_{1-8}$-alkylene-, —C$_{1-8}$-alkenylene- and C$_{1-8}$-alkinylene.

Aliphatic means preferably respectively a branched or unbranched, saturated or a mono- or polyunsaturated, unsubstituted or mono- or polysubstituted, aliphatic hydrocarbon residue. Where aliphatic is mono- or polysubstituted, the substituents are selected independently of one another from the group comprising —F, —Cl, —Br, —I, —CN, —NO$_2$, —CHO, =O, —R$^Z$, —C(=O)R$^Z$, —C(=O)H, —C(=O)OH, —C(=O)OR$^Z$, —C(=O)NH$_2$, —C(=O)NHR$^Z$, —C(=O)N(R$^Z$)$_2$, —OH, —OR$^Z$, —OC(=O)H, —OC(=O)R$^Z$, —OC(=O)OR$^Z$, —OC(=O)NHR$^Z$, —OC(=O)N(R$^Z$)$_2$, —SH, —SR$^Z$, —SO$_3$H, —S(=O)$_{1-2}$—R$^Z$, —S(=O)$_{1-2}$NH$_2$, —NH$_2$, —NHR$^Z$, —N(R$^Z$)$_2$, —N$^+$(R$^Z$)$_3$, —N$^+$(R$^Z$)$_2$O$^-$, —NHC(=O)R$^Z$, —NHC(=O)OR$^Z$, —NHC(=O)NH$_2$, —NHC(=O)NHR$^Z$, —NHC(=O)—N(R$^Z$)$_2$, —Si(R$^Z$)3 or —PO(OR$^Z$)$_2$.

Thus, "aliphatic" covers acyclic saturated or unsaturated hydrocarbon residues that can be branched or straight-chain, i.e. alkanyls, alkenyls and alkinyls. In this case, alkenyls have at least one C=C double bond and alkinyls have at least one C≡C triple bond. Preferred unsubstituted monovalent aliphatics comprise —CH$_3$, —CH$_2$CH$_3$, —CH$_2$CH$_2$CH$_3$, —CH(CH$_3$)$_2$, —CH$_2$CH$_2$CH$_2$CH$_3$, —CH(CH$_3$)CH$_2$CH$_3$, —CH$_2$CH(CH$_3$)$_2$, —C(CH$_3$)$_3$, —CH$_2$CH$_2$CH$_2$—CH$_2$CH$_3$ and —CH$_2$CH$_2$CH$_2$CH$_2$CH$_2$CH$_3$; but also —CH=CH$_2$, —C≡CH, —CH$_2$CH=CH$_2$, —CH=CHCH$_3$, —CH$_2$C≡CH, —C≡CCH$_3$ and —CH=CHCH=CH$_2$. Preferred unsubstituted bivalent aliphatics comprise —CH$_2$—, —CH$_2$CH$_2$—, —CH$_2$CH(CH$_3$)—, —CH(CH$_3$)—CH$_2$—, —CH$_2$CH$_2$CH$_2$—, —CH(CH$_3$)CH$_2$CH$_2$—, —CH$_2$CH(CH$_3$)—CH$_2$—, —CH$_2$CH$_2$CH(CH$_3$)—, —CH-(CH$_2$CH$_3$)CH$_2$— and —CH$_2$CH$_2$—CH$_2$CH$_2$—; but also —CH=CH—, —C≡C—, —CH$_2$CH=CH—, —CH=CHCH$_2$—, —CH$_2$C≡C— and —C≡CCH$_2$—. Preferred substituted monovalent aliphatics comprise —CH$_2$F, —CHF$_2$, —CF$_3$, —CH$_2$CF$_3$, —CF$_2$CF$_3$, —CH$_2$OH, —CH$_2$CH$_2$OH, —CH$_2$CHOHCH$_3$, —CH$_2$CHOH$_2$, —CH$_2$CH$_2$OCH$_3$ and —CH$_2$N(CH$_3$)$_2$. Preferred substituted bivalent aliphatics comprise —CF$_2$—, —CF$_2$CF$_2$—, —CH$_2$CHOH—, —CHOHCH$_2$— and —CH$_2$CHOHCH$_2$—. -Methyl-, -ethyl-, -n-propyl- and -n-butyl- are particularly preferred.

Cycloaliphatic means preferably respectively a saturated or a mono- or polyunsaturated, unsubstituted or mono- or polysubstituted, aliphatic (i.e. not aromatic), mono- or multicyclic hydrocarbon residue. The number of ring-carbon atoms preferably lies in the specified range (i.e. a "C$_{3-12}$-cycloaliphatic" preferably has 3, 4, 5, 6, 7, 8, 9, 10, 11 or 12 ring-carbon atoms). For the purposes of the description "C$_{3-12}$-cycloaliphatic" is preferably a cyclic hydrocarbon with 3, 4, 5, 6, 7, 8, 9, 10, 11 or 12 ring-carbon atoms, saturated or unsaturated, but not aromatic, wherein possibly one or two carbon atoms are replaced independently of one another by a heteroatom S, N or O. Where cycloalkyl is mono- or polysubstituted, the substituents are selected independently of one another from the group comprising —F, —Cl, —Br, —I, —CN, —NO$_2$, —CHO, =O, —R$^Z$, —C(=O)R$^Z$, —C(=O)H, —C(=O)OH, —C(=O)OR$^Z$, —C(=O)NH$_2$, —C(=O)NHR$^Z$, —C(=O)N(R$^Z$)$_2$, —OH, —OR$^Z$, —OC(=O)H, —OC(=O)R$^Z$, —OC(=O)—OR$^Z$, —OC(=O)NHR$^Z$, —OC(=O)N(R$^Z$)$_2$, —SH, —SR$^Z$, —SO$_3$H, —S(=O)$_{1-2}$—R$^Z$, —S(=O)$_{1-2}$NH$_2$, —NH$_2$, —NHR$^Z$, —N(R$^Z$)$_2$, —N$^+$(R$^Z$)$_3$, —N$^+$(R$^Z$)$_2$O$^-$, —NHC(=O)R$^Z$, —NHC(=O)OR$^Z$, —NHC(=O)NH$_2$, —NHC(=O)NHR$^Z$, —NHC(=O)—N(R$^Z$)$_2$, —Si(R$^Z$)$_3$ or —PO(OR$^Z$)$_2$.

Preferably, C$_{3-12}$-cycloaliphatic is selected from the group comprising cyclopropyl, cyclobutyl, cyclopentyl, cyclohexyl, cycloheptyl, cyclooctyl, cyclononyl, cyclodecyl, cycloundecyl, cyclododecyl, cyclopentenyl, cyclohexenyl, cycloheptenyl, cyclooctenyl, cyclononenyl, cyclodecenyl, cycloundecenyl, cyclododecenyl, but also tetrahydropyranyl, dioxanyl, dioxolanyl, morpholinyl, piperidinyl, piperazinyl, pyrazolinonyl and pyrrolidinyl.

In association with "aliphatic" or "cycloaliphatic", "mono- or polysubstituted" is preferably understood to mean the mono- or polysubstitution, e.g. the mono-, di-, tri- or 4-substitution, of one or more hydrogen atoms by —F, —Cl, —Br, —I, —OH, —OC$_{1-8}$-alkyl, —OC(=O)C$_{1-8}$-alkyl, —SH, —NH$_2$, —NHC$_{1-8}$-alkyl, —N(C$_{1-8}$-alkyl)$_2$, —C(=O)OC$_{1-8}$-alkyl or —C(=O)OH. Particularly preferred substituents are —F, —Cl, —OH, —SH, —NH$_2$ and —C(=O)OH.

Polysubstituted residues are understood to be those residues that are polysubstituted, e.g. twice or three times either at different or at the same atoms, e.g. three times at the same C-atom, as in the case of —CF$_3$ or —CH$_2$CF$_3$, or at different sites, as in the case of —CH(OH)—CH=CH—CHCl$_2$. The polysubstitution can occur with the same or with different substituents. A substituent may also be substituted itself. Thus, —O— aliphatic also covers —OCH$_2$CH$_2$O—CH$_2$CH$_2$OH, amongst others. It is preferred if aliphatic or cycloaliphatic is substituted with —F, —Cl, —Br, —I, —CN, —CH$_3$, —C$_2$H$_5$, —NH$_2$, —NO$_2$, —SH, —CF$_3$, —OH, —OCH$_3$, —OC$_2$H$_5$ or —N(CH$_3$)$_2$. It is most particularly preferred if aliphatic or cycloaliphatic is substituted with —OH, —OCH$_3$ or —OC$_2$H$_5$.

Aryl preferably respectively independently stands for a carbocyclic ring system with at least one aromatic ring, but without heteroatoms in this ring, wherein the aryl residues can possibly be condensed with further saturated, (partially) unsaturated or aromatic ring systems and each aryl residue can be present in unsubstituted or mono- or polysubstituted form, wherein the aryl substituents are the same or different and can be in any desired and possible position of the aryl. Preferred aryls are phenyl, naphthyl, anthracenyl, phenanthrenyl, fluoroanthenyl, fluoroenyl, indanyl and tetralinyl. Phenyl and naphthyl are particularly preferred. Where aryl is mono- or polysubstituted, the aryl substituents can be the same or different and be in any desired and possible position of the aryl, and are selected independently of one another from the group comprising —F, —Cl, —Br, —I, —CN, —NO$_2$, —CHO, =O, —R$^Z$, —C(=O)R$^Z$, —C(=O)H, —C(=O)OH, —C(=O)OR$^Z$, —C(=O)NH$_2$, —C(=O)NHR$^Z$, —C(=O)—N(R$^Z$)$_2$, —OH, —O(CH$_2$)$_{1-2}$O—, —OR$^Z$, —OC(=O)H, —OC(=O)R$^Z$, —OC(=O)OR$^Z$, —OC(=O)NHR$^Z$, —OC(=O)N(R$^Z$)$_2$, —SH, —SR$^Z$, —SO$_3$H, —S(=O)$_{1-2}$—R$^Z$, —S(=O)$_{1-2}$NH$_2$, —NH$_2$, —NHR$^Z$, —N(R$^Z$)$_2$, —N$^+$(R$^Z$)$_3$, —N$^+$(R$^Z$)$_2$O$^-$, —NHC(=O)R$^Z$, —NHC(=O)OR$^Z$, —NH—C(=O)NH$_2$, —NHC(=O)NHR$^Z$, —NHC(=O)—N(R$^Z$)$_2$, —Si(R$^Z$)$_3$ and —PO(OR$^Z$)$_2$; wherein if necessary N-ring atoms present can be respectively oxidized. Preferred substituted aryls are 2-fluorophenyl, 3-fluorophenyl, 4-fluorophenyl, 2,3-difluorophenyl, 2,4-difluorophenyl, 3,4-difluorophenyl, 2-chlorophenyl, 3-chlorophenyl, 4-chlorophenyl, 2,3-dichlorophenyl, 2,4-dichlorophenyl, 3,4-dichlorophenyl, 2-methoxy-phenyl, 3-methoxy-phenyl, 4-methoxy-phenyl, 2,3-dimethoxy-phenyl, 2,4-dimethoxy-phenyl, 3,4-dimethoxy-phenyl, 2-methyl-phenyl, 3-methyl-phenyl, 4-methyl-phenyl, 2,3-dimethyl-phenyl, 2,4-dimethyl-phenyl and 3,4-dimethyl-phenyl.

Heteroaryl preferably stands for a 5-, 6- or 7-membered cyclic aromatic residue that contains 1, 2, 3, 4 or 5 heteroatoms, wherein the heteroatoms, the same or different, are nitrogen, oxygen or sulphur, and the heterocycle can be unsubstituted or mono- or polysubstituted; wherein in the case of the substitution on the heterocycle, the substituents can be the same or different and can be in any desired and possible position of the heteroaryl; and wherein the heterocycle can also be part of a bi- or polycyclic system. "Heteroaryl" is preferably selected from the group comprising pyrrolyl, indolyl, furyl (furanyl), benzofuranyl, thienyl (thiophenyl), benzothienyl, benzothiadiazolyl, benzooxadiazolyl, benzothiazolyl, benzooxazolyl, benzotriazolyl, benzodioxolanyl, benzodioxanyl, phthalazinyl, pyrazolyl, imidazolyl, thiazolyl, oxazolyl, isoxazoyl, pyridinyl, pyridazinyl, pyrimidinyl, pyrazinyl, pyranyl, indazolyl, purinyl, indolizinyl, quinolinyl, isoquinolinyl, quinazolinyl, carbazolyl, phenazinyl, phenothiazinyl or oxadiazolyl, wherein the bonding can occur via any desirable and possible ring member of the heteroaryl residue. Where heteroaryl is mono- or polysubstituted, the heteroaryl substituents can be the same or different and can be in any desirable and possible position of the heteroaryl, and are selected independently of one another from the group comprising —F, —Cl, —Br, —I, —CN, —NO$_2$, —CHO, =O, —R$^Z$, —C(=O)R$^Z$, —C(=O)H, —C(=O)OH, —C(=O)OR$^Z$, —C(=O)NH$_2$, —C(=O)NHR$^Z$, —C(=O)—N(R$^Z$)$_2$, —OH, —O(CH$_2$)$_{1-2}$O—, —OR$^Z$, —OC(=O)H, —OC(=O)R$^Z$, —OC(=O)OR$^Z$, —OC(=O)NHR$^Z$, —OC(=O)N(R$^Z$)$_2$, —SH, —SR$^Z$, —SO$_3$H, —S(=O)$_{1-2}$—R$^Z$, —S(=O)$_{1-2}$NH$_2$, —NH$_2$, —NHR$^Z$, —N(R$^Z$)$_2$, —N$^+$(R$^Z$)$_3$, —N$^+$(R$^Z$)$_2$O$^-$, —NHC(=O)R$^Z$, —NHC(=O)OR$^Z$, —NH—C(=O)NH$_2$, —NHC(=O)NHR$^Z$, —NHC(=O)—N(R$^Z$)$_2$, —Si(R$^Z$)$_3$ and —PO(OR$^Z$)$_2$; wherein if necessary N-ring atoms present can be respectively oxidized.

Regarding "aryl" or "heteroaryl", "mono- or polysubstituted" are understood to mean the mono- or polysubstitution, e.g. di-, tri-, 4- or 5-substitution, of one or more hydrogen atoms of the ring system.

Particularly preferred are the (hetero)aryl substituents selected independently of one another from —F, —Cl, —Br, —I, —CN, —CHO, —CO$_2$H, —NH$_2$, —NO$_2$, —NHR$^Z$, —N(R$^Z$)$_2$, —N$^+$(R$^Z$)$_3$, —N$^+$(R$^Z$)$_2$O$^-$, —SH, —SR$^Z$, —OH, —OR$^Z$, —C(=O)R$^Z$, —CO$_2$R$^Z$, —C(=O)NH$_2$, —C(=O)NHR$^Z$, —C(=O)N(R$^Z$)$_2$, —S(=O)$_{1-2}$R$^Z$, —S(=O)$_2$NH$_2$, —SO$_3$H, =O or —R$^Z$. Preferred substituents are —F, —Cl, —Br, —I, —OH, —OC$_{1-8}$-alkyl, —O—C(=O)—C$_{1-8}$-alkyl, —SH, —NH$_2$, —NHC$_{1-8}$-alkyl, —N(C$_{1-8}$-alkyl)$_2$, —C(=O)OC$_{1-8}$-alkyl or —C(=O)OH. Particularly preferred substituents are —F, —Cl, —OH, —SH, —NH$_2$ and —C(=O)OH.

Unless expressly stated otherwise, residues having more than a single binding partner can be attached in any direction. For example, the residue "—S—(CH$_2$)—C(=O)—" which is attached to binding partners B$_1$ and B$_2$ can be present in either direction, B$_1$—S—(CH$_2$)—C(=O)—B$_2$ or B$_1$—C(=O)—(CH$_2$)—S—B$_2$.

The compounds according to the invention can be present in the form of a single stereoisomer or mixture thereof, the free compounds and/or their physiologically acceptable salts and/or solvates.

The compounds according to the invention can be chiral or achiral, depending on the substitution pattern.

If the compounds according to the invention are chiral, then they are preferably present as racemate or a mixture of stereoisomers or diastereomers or in enriched form of an enantiomer. In a preferred embodiment the enantiomer excess (ee) of the S-enantiomer amounts to at least 50% ee, more preferred at least 75% ee, more preferred at least 90% ee, most preferred at least 95% ee, and in particular at least 99% ee. In another preferred embodiment, the enantiomer excess (ee) of the R-enantiomer amounts to at least 50% ee, more preferred at least 75% ee, more preferred at least 90% ee, most preferred at least 95% ee, and in particular at least 99% ee.

Suitable methods for separating the enantiomers are known to the person skilled in the art. Preparative HPLC on chiral stationary phases and conversion into diastereomeric intermediates can be given as examples. The conversion into diastereomeric intermediates can occur, for example, as salt formation by means of chiral, enantiomer-pure acids. After separation of the diastereomers thus formed, the salt can then be converted into the free base or another salt again.

Unless expressly specified, each reference to the compounds according to the invention covers all isomers in pure form and admixture with one another (e.g. stereoisomers, diastereomers, enantiomers) in any desired mixture ratio.

Unless expressly specified, each reference to the compounds according to the invention covers the free compounds (i.e. the forms that are not present in the form of salt) and all physiologically acceptable salts.

For the purposes of the description, physiologically acceptable salts of the compounds according to the invention are present as salts with anions or acids of the respective compound with inorganic or organic acids, which are physiologically acceptable—in particular on application in humans and/or mammals.

Examples of physiologically acceptable salts of specific acids are salts of: hydrochloric acid, hydrobromic acid, sulphuric acid, methane sulphonic acid, formic acid, acetic acid, oxalic acid, succinic acid, malic acid, tartaric acid, mandelic acid, fumaric acid, lactic acid, citric acid, glutamic acid, saccharinic acid, monomethyl sebacic acid, 5-oxo-proline, hexane-1-sulphonic acid, nicotinic acid, 2-, 3- or 4-aminobenzoic acid, 2,4,6-trimethyl benzoic acid, α-liponic acid, acetylglycine, acetylsalicylic acid, hippuric acid and/or aspartic acid. The hydrochloride, citrate and hemicitrate are particularly preferred.

Physiologically acceptable salts with cations or bases are salts of the respective compound—as anion with at least one, preferably inorganic, cation, which are physiologically acceptable—in particular on application in humans and/or mammals Particularly preferred are the salts of the alkali and earth alkali metals, also ammonium salts, but in particular (mono-) or (di-) sodium, (mono-) or (di-) potassium, magnesium or calcium salts.

The compounds according to the invention are defined by substituents, e.g. by $R^1$, $R^2$ and $R^3$ (substituents of the first generation), which are themselves possibly substituted (substituents of the second generation). Depending on the definition, these substituents of the substituents can themselves be substituted again (substituents of the third generation). If, for example, $R^1$=—$R^Z$, wherein —$R^Z$=—$C_{1-8}$-aliphatic (substituent of the first generation), then —$C_{1-8}$-aliphatic can itself be substituted, e.g. with —$OR^Z$, wherein $R^Z$=-aryl (substituent of the second generation). This gives the functional group —$C_{1-8}$-aliphatic-O-aryl. -Aryl can then in turn be substituted again, e.g. with —Cl (substituent of the third generation). This then gives overall the functional group —$C_{1-8}$-aliphatic-O-aryl-Cl.

Another aspect of the invention relates to the compounds according to the invention as described above as medicaments.

Another aspect of the invention relates to pharmaceutical compositions or pharmaceutical dosage forms comprising the compounds according to the invention as described above.

Preferably, the pharmaceutical compositions comprise a compound according to the invention as described above, and a pharmaceutically acceptable carrier. The term "pharmaceutically acceptable carrier," as used herein, means a non-toxic, inert solid, semi-solid or liquid filler, diluent, encapsulating material or formulation auxiliary of any type.

Some examples of materials which may serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; cocoa butter and suppository waxes; oils such as peanut oil, cottonseed oil, safflower oil, sesame oil, olive oil, corn oil and soybean oil; glycols; such a propylene glycol; esters such as ethyl oleate and ethyl laurate; agar; buffering agents; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as releasing agents, coloring agents, coating agents, sweetening, flavoring and perfuming agents, preservatives and antioxidants may also be present in the composition, according to the judgment of one skilled in the art of formulations.

The pharmaceutical compositions may be administered to subjects (e.g., humans and other mammals) orally, rectally, parenterally, intravaginally, intracisternally, intraperitoneally, topically (as by powders, ointments or drops), bucally, extracorporeally, e.g. by dialysis, or as an oral or nasal spray. The term "parenterally," as used herein, refers to modes of administration, including intravenous, intramuscular, intraperitoneal, intrasternal, subcutaneous, intraarticular injection and infusion.

Pharmaceutical compositions for parenteral injection comprise pharmaceutically acceptable sterile aqueous or nonaqueous solutions, dispersions, suspensions or emulsions and sterile powders for reconstitution into sterile injectable solutions or dispersions. Examples of suitable aqueous and nonaqueous carriers, diluents, solvents or vehicles include water, ethanol, polyols (polyethylene glycol, propylene glycol, glycerol, and the like, and suitable mixtures thereof), vegetable oils (such as olive oil) and injectable organic esters such as ethyl oleate, or suitable mixtures thereof. Suitable fluidity of the composition may be maintained, for example, by the use of a coating such as lecithin, by the maintenance of the required particle size in the case of dispersions, and by the use of surfactants.

These compositions may also contain adjuvants, such as preservative agents, wetting agents, emulsifying agents, and dispersing agents. Prevention of the action of microorganisms may be ensured by various antibacterial and antifungal agents, for example, parabens, phenol, chlorobutanol, sorbic acid, and the like. It also may be desirable to include isotonic agents, for example, sugars, sodium chloride and the like. Prolonged absorption of the injectable pharmaceutical form may be brought about by the use of agents delaying absorption, for example, aluminum monostearate and gelatin.

In some cases, in order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug may depend upon its rate of dissolution, which, in turn, may depend upon crystal size and crystalline form. Alternatively, a parenterally administered drug form may be administered by dissolving or suspending the drug in an oil vehicle.

Suspensions, in addition to the active compounds, may contain suspending agents, for example, polyoxyethylene sorbitol, ethoxylated isostearyl alcohols, and sorbitan esters, microcrystalline cellulose, aluminum metahydroxide, bentonite, agar-agar, tragacanth, and mixtures thereof.

If desired, and for more effective distribution, the compounds may be incorporated into slow-release or targeted-delivery systems such as polymer matrices, liposomes, and microspheres. They may be sterilized, for example, by filtration through a bacteria-retaining filter or by incorporation of sterilizing agents in the form of sterile solid compositions, which may be dissolved in sterile water or some other sterile injectable medium immediately before use.

Injectable depot forms are made by forming microencapsulated matrices of the drug in biodegradable polymers such as polylactide-polyglycolide. Depending upon the ratio of drug to polymer and the nature of the particular polymer employed, the rate of drug release may be controlled. Depot injectable formulations also are prepared by entrapping the drug in liposomes or microemulsions which are compatible with body tissues.

The injectable formulations may be sterilized, for example, by filtration through a bacterial-retaining filter or by incorporating sterilizing agents in the form of sterile solid compositions which may be dissolved or dispersed in sterile water or other sterile injectable medium just prior to use.

Injectable preparations, for example, sterile injectable aqueous or oleaginous suspensions may be formulated according to the known art using suitable dispersing or wetting agents, suspending agents and the like. The sterile injectable preparation also may be a sterile injectable solution, suspension or emulsion in a nontoxic, parenterally acceptable diluent or solvent such as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose, any bland fixed oil may be employed including synthetic mono- or diglycerides. In addition, fatty acids such as oleic acid are used in the preparation of injectables.

Solid dosage forms for oral administration include, but are not limited to, capsules, tablets, pills, powders, and granules. In such solid dosage forms, one or more compounds is mixed with at least one inert pharmaceutically acceptable carrier such as sodium citrate or dicalcium phosphate and/or a) fillers or extenders such as starches, lactose, sucrose, glucose, mannitol, and salicylic acid; b) binders such as carboxymethylcellulose, alginates, gelatin, polyvinylpyrrolidinone, sucrose, and acacia; c) humectants such as glycerol; d) disintegrating agents such as agar-agar, calcium carbonate, potato or tapioca starch, alginic acid, certain silicates, and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay; and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using lactose or milk sugar as well as high molecular weight polyethylene glycols.

The solid dosage forms of tablets, dragees, capsules, pills, and granules may be prepared with coatings and shells such as enteric coatings and other coatings well-known in the pharmaceutical formulating art. They optionally may contain opacifying agents and also may be of a composition that they release the active ingredient(s) only, or preferentially, in a certain part of the intestinal tract in a delayed manner. Examples of materials useful for delaying release of the active agent may include polymeric substances and waxes.

Compositions for rectal or vaginal administration are preferably suppositories which may be prepared by mixing the compounds with suitable non-irritating carriers such as cocoa butter, polyethylene glycol or a suppository wax which are solid at ambient temperature but liquid at body temperature and therefore melt in the rectum or vaginal cavity and release the active compound.

Liquid dosage forms for oral administration may include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions may also include adjuvants such as wetting agents, emulsifying and suspending agents, sweetening, flavoring, and perfuming agents.

Suspensions, in addition to the active compounds, may contain suspending agents, for example, ethoxylated isostearyl alcohols, polyoxyethylene sorbitol and sorbitan esters, microcrystalline cellulose, aluminum metahydroxide, bentonite, agar-agar, tragacanth, and mixtures thereof.

If desired, and for more effective distribution, the compounds may be incorporated into slow-release or targeted-delivery systems such as polymer matrices, liposomes, and microspheres. They may be sterilized, for example, by filtration through a bacteria-retaining filter or by incorporation of sterilizing agents in the form of sterile solid compositions, which may be dissolved in sterile water or some other sterile injectable medium immediately before use.

Dosage forms for topical or transdermal administration of a compound include ointments, pastes, creams, lotions, gels, powders, solutions, sprays, inhalants or patches. A desired compound is admixed under sterile conditions with a pharmaceutically acceptable carrier and any needed preservatives or buffers as may be required. Ophthalmic formulation, eardrops, eye ointments, powders and solutions are also contemplated as being within the scope of this disclosure.

The ointments, pastes, creams and gels may contain, in addition to an active compound, animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays may contain, in addition to the compounds, lactose, talc, silicic acid, aluminum hydroxide, calcium silicates and polyamide powder, or mixtures of these substances. Sprays additionally may contain customary propellants such as chlorofluorohydrocarbons.

Compounds also may be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes may be used. The present compositions in liposome form may contain, in addition to the compounds, stabilizers, preservatives, and the like. The preferred lipids are the natural and synthetic phospholipids and phosphatidylcholines (lecithins) used separately or together. Methods to form liposomes are known in the art.

Dosage forms for topical administration of a compound according to the invention as described above include powders, sprays, ointments and inhalants. The active compound is mixed under sterile conditions with a pharmaceutically acceptable carrier and any needed preservatives, buffers or propellants. Ophthalmic formulations, eye ointments, powders and solutions are also possible. Aqueous liquid compositions may also be useful.

The compounds according to the invention are preferably administered once daily, twice daily, thrice daily or more often to a subject in need thereof.

The compounds according to the invention are preferably administered orally, rectally, intravenously, intramuscularly, intraperitoneally, intrasternally, subcutaneously, by intraarticular injection, by infusion, intravaginally, intracisternally, intraperitoneally, topically, bucally or extracorporeally.

In some cases it is of advantage to treat a patient with a combination of cancer medicaments to achieve the desired remission of cancer cells. The need for such a combination of cancer medicaments, i.e. a combination therapy, particularly arises when cancer cells are or become resistant to conventional cancer medicaments such as e.g. tyrosine-kinase inhibitors. Such a resistance to conventional cancer medicaments has for example been observed in lung cancer cells which may exhibit a resistance to tyrosine-kinase inhibitors after the patient has been treated with tyrosine-kinase inhibitors for a while.

Another aspect of the invention relates to a pharmaceutical composition comprising a combination of
a compound according to general formula (1) and
a second pharmacologically active compound.

Preferably, the second pharmacologically active compound is a tyrosine-kinase inhibitor, more preferred the second pharmacologically active compound is selected from the group consisting of Imatinib, Gefitinib, Erlotinib, Sunitinib and Cabozantinib.

Preferably, the combination of a compound according to general formula (1) and a second pharmacologically active compound is used in the treatment of cancer, more preferred in the treatment of drug resistant cancer, even more preferred in the treatment of cancer selected from the group consisting of tyrosine-kinase inhibitor (TM) resistant EGFR and KRAS mutant cancers.

Particularly preferred is the use of the combination of a compound according to general formula (1) and a second pharmacologically active compound in the treatment of cancer selected from the group consisting of lung cancer, brain cancer, eye cancer, oral cancer, throat cancer, tongue cancer, trachea cancer, stomach cancer, liver cancer, kidney cancer, pancreatic cancer, gallbladder cancer, colorectal cancer, cancer of the urinary tract, bladder cancer, testicular cancer, ovarian cancer, cervical cancer, endometrial cancer, pancreatic cancer, skin cancer, Hodgkin's lymphoma, non-Hodgkin's lymphoma, breast cancer, and prostate cancer.

Most preferred is the use of the combination of a compound according to general formula (1) and a second pharmacologically active compound in the treatment of lung cancer, particularly non-small cell lung cancer (NSCLC).

All aspects of a pharmaceutical composition comprising the compounds according to the invention as described above also apply to the pharmaceutical composition comprising a combination of a compound according to general formula (1) and a second pharmacologically active compound.

Another aspect of the invention relates to a kit comprising
a first pharmaceutical composition comprising a compound according to general formula (1) and
a second pharmaceutical composition comprising a second pharmacologically active compound;
wherein the first pharmaceutical composition and the second pharmaceutical composition are separate of one another.

Preferably, the first pharmaceutical composition and the second pharmaceutical composition of said kit are for administration through the same route. In another embodiment of the invention, the first pharmaceutical composition is for administration through a different route than the second pharmaceutical composition.

Preferred administration routes for the first and second pharmaceutical composition of said kit are oral, rectal parenteral, intravaginal, intracisternal, intraperitoneal, topical or bucal administration to a patient.

Preferably, the first pharmaceutical composition and the second pharmaceutical composition of said kit are administered to a patient subsequent to each other, wherein
the first pharmaceutical composition is administered first, followed by administration of the second pharmaceutical composition, or
the second pharmaceutical composition is administered first, followed by administration of the first pharmaceutical composition.

It is preferred that the period of time between the administration of the first pharmaceutical composition and the second pharmaceutical composition, or vice versa, is at least 1 hour, at least 2 hours, at least 3 hours, at least 4 hours or at least 5 hours.

More preferred, the period of time between the administration of the first pharmaceutical composition and the second pharmaceutical composition, or vice versa, is at least 1 day, at least 2 days, at least 3 days, at least 4 days, at least 5 days, at least 6 days, at least 7 days or at least 8n days.

More preferred, the period of time between the administration of the first pharmaceutical composition and the second pharmaceutical composition, or vice versa, is at least 2 weeks, at least 3 weeks, at least 4 weeks, at least 5 weeks, at least 6 weeks or at least 7 weeks or at least 8 weeks.

Preferably, the second pharmacologically active compound of said kit is a tyrosine-kinase inhibitor, more preferably the second pharmacologically active compound of said kit is selected from the group consisting of Imatinib, Gefitinib, Erlotinib, Sunitinib and Cabozantinib.

Preferably, the kit is used in the treatment of cancer, more preferred in the treatment of drug resistant cancer, even more preferred in the treatment of cancer selected from the group consisting of tyrosine-kinase inhibitor (TKI) resistant EGFR and KRAS mutant cancers.

Particularly preferred is the use of the kit in the treatment of cancer selected from the group consisting of lung cancer, brain cancer, eye cancer, oral cancer, throat cancer, tongue cancer, trachea cancer, stomach cancer, liver cancer, kidney cancer, pancreatic cancer, gallbladder cancer, colorectal cancer, cancer of the urinary tract, bladder cancer, testicular cancer, ovarian cancer, cervical cancer, endometrial cancer, pancreatic cancer, skin cancer, Hodgkin's lymphoma, non-Hodgkin's lymphoma, breast cancer, and prostate cancer.

Most preferred is the use of the kit in the treatment of lung cancer, particularly non-small cell lung cancer (NSCLC).

All aspects of a pharmaceutical composition comprising the compounds according to the invention as described above also apply to the first pharmaceutical composition and the second pharmaceutical composition of said kit.

In a further embodiment, the invention relates to the use of a compound according to the invention for the manufacture of a medicament for use in treatment of cancer, preferably selected from the group consisting of tyrosine-kinase inhibitor (TKI) resistant EGFR and KRAS mutant cancers, drug resistant cancer, breast cancer and lung cancer.

In a yet further embodiment, the invention relates to a method of treating cancer, preferably selected from the group consisting of tyrosine-kinase inhibitor (TKI) resistant EGFR and KRAS mutant cancers, drug resistant cancer, breast cancer and lung cancer, which comprises administering an effective amount of at least one compound according to the invention to a subject in need thereof.

A yet further aspect of the invention relates to the following compounds as such

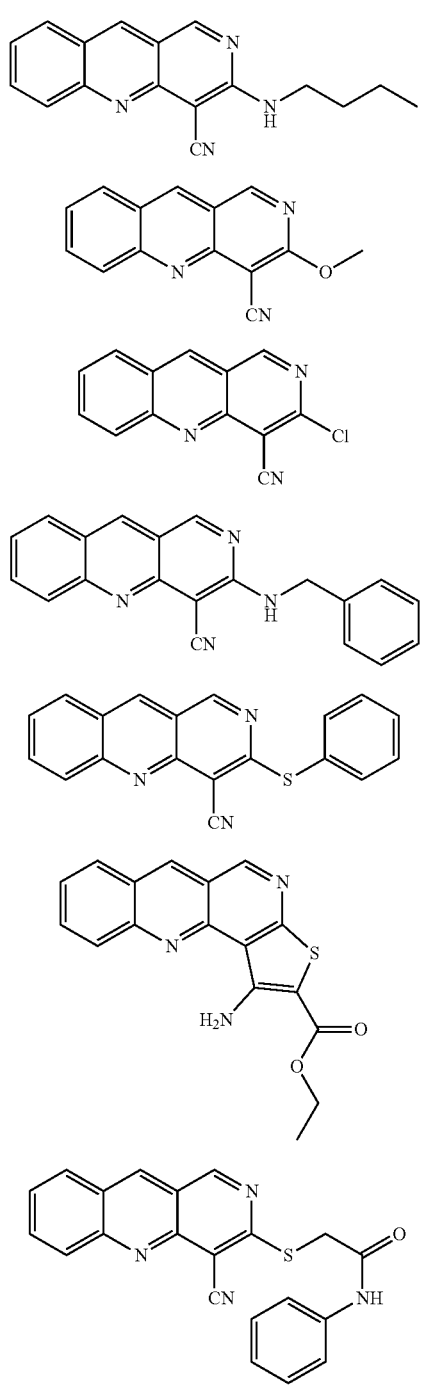

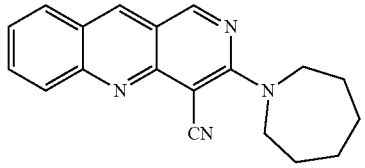

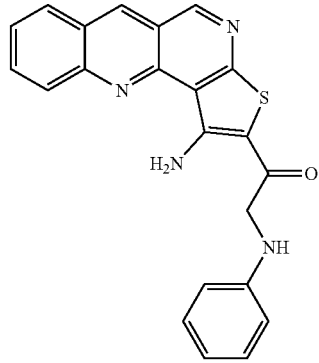

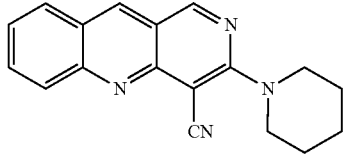

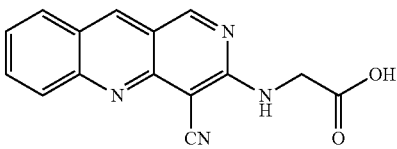

or a physiologically acceptable salt thereof.

In a preferred embodiment, the invention relates to compounds (A), (B), (D), (E), (G), (H), (I), (J), (K), (L) and (M) or a physiologically acceptable salt thereof, for use as medicine.

Figure 22:
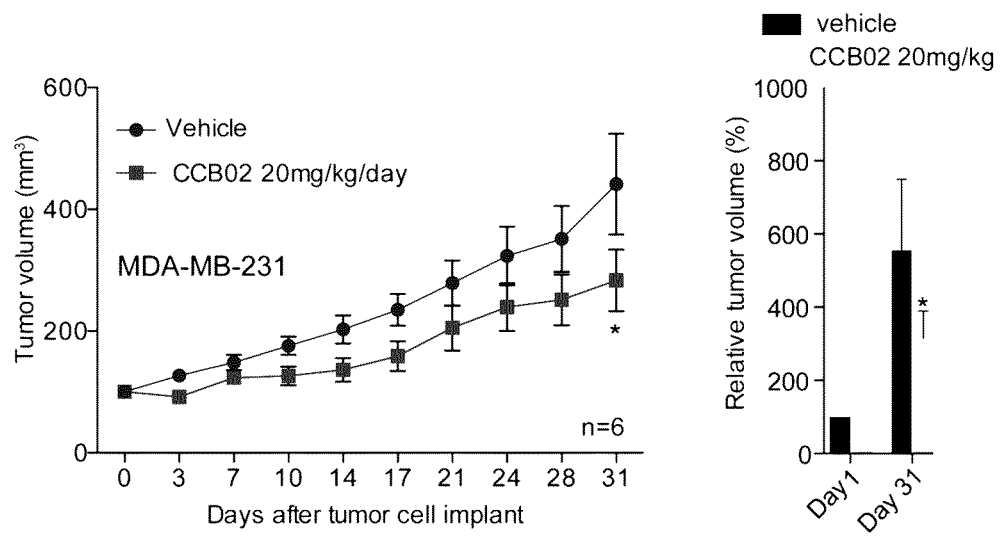
Figure 23:
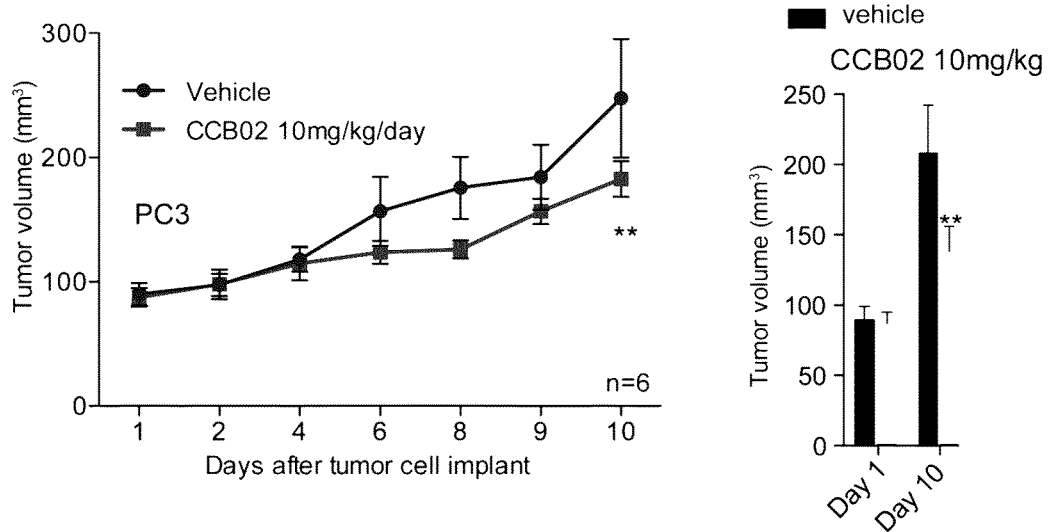

FIGS. 22 and 23 show the anti-tumor activity of compound (B) with respect to control after 10 (for PC3) and 31 (for MDA-MB-231) days.

Figure 24:
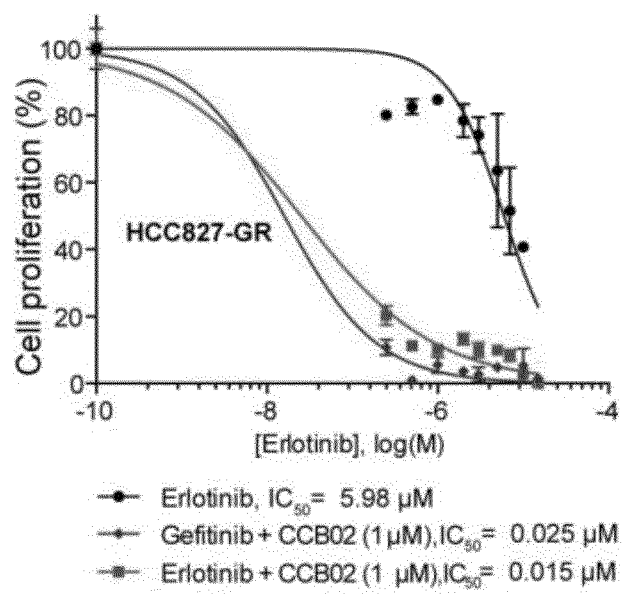
Figure 25:
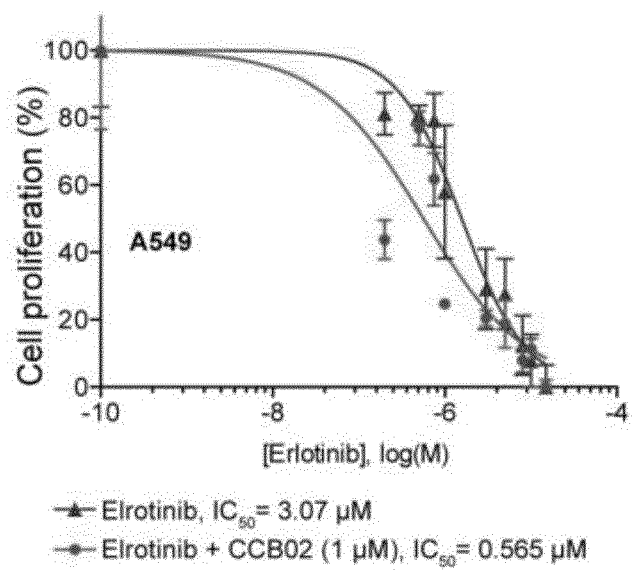

FIGS. 24 and 25 show dose response curves of combination therapy with conventional cancer drugs and compound (B) compared to therapy with only one conventional cancer drug.

Figure 26:
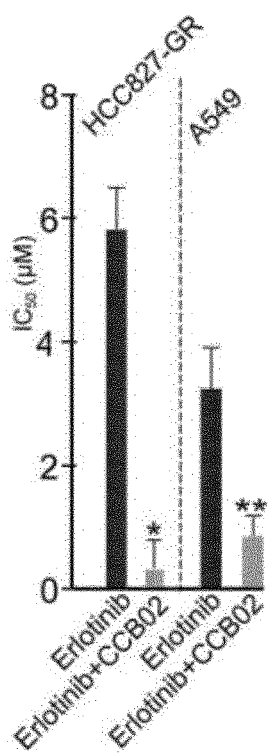

FIG. 26 shows $IC_{50}$ values of TKI resistant (NSCLC) lung cancer cell lines treated with combination therapy compared to therapy with only one conventional cancer drug.

Figure 27:
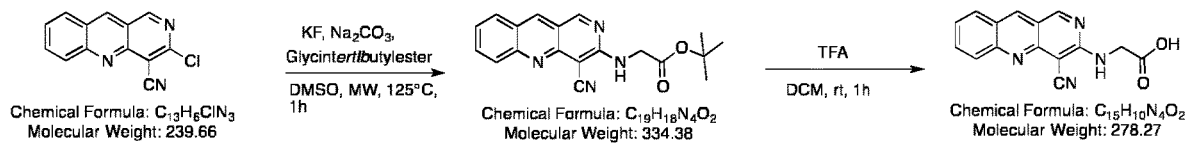

FIG. 27 shows a scheme to synthesize compound (M).

The following examples further illustrate the invention but are not to be construed as limiting its scope.

EXAMPLE 1

Studies in *Drosophila* have shown that free-tubulin dimers negatively regulate the microtubule nucleating activity of centrosomes through its direct interaction with the conserved centrosomal protein Sas-4/CPAP. Specifically, *Drosophila* carrying a mutated Sas-4, which cannot interact with tubulin, prematurely activated interphase centrosomes to nucleate robust microtubules suggesting that tubulin can function as a molecular switch in regulating centrosome activity. The subsequent CPAP-tubulin crystal structure identified that CPAP forms a high-affinity CPAP-tubulin complex via a conserved phenylalanine (F375) of its tubulin-binding domain.

EXAMPLE 2

Building on Example 1, a proof-of-principle experiment was established in which lentiviral-mediated transduction of constitutive or doxycycline-inducible $CPAP^{F375A}$ that cannot interact with tubulin (hereafter CPAPΔT) was introduced into non-transformed human mammary epithelial MCF10A cells. These MCF10A cells are engineered to regulate centrosome amplification via doxycycline-inducible overexpression of Polo-Like-Kinase (PLK4). Introducing CPAPΔT prematurely activated Plk4-induced extra-centrosomes in interphase to nucleate microtubules and prevented them from clustering.

As a result, the prematurely nucleating extra-centrosomes caused multi-polar spindles as cells progressed into mitosis. Strikingly, CPAPΔT cells resided in mitosis ~10 times much longer than control cells and eventually underwent apoptosis as characterized by the formation of apoptopic blebs.

These results demonstrate that premature activation of extra-centrosomes could cause multipolar mitosis and mitotic catastrophe. Importantly, expressing CPAPΔT in cells that do not carry extra-centrosomes did not display any of these effects.

EXAMPLE 3

CPAPΔT was introduced in breast cancer (MDA-MB-231) and EGFR tyrosine-kinase inhibitor (TKI) resistant EGFR T790M mutant NSCLC cells ($H1975^{T790M}$) and it was found that these cells exclusively underwent premature centrosome activation, centrosome declustering in interphase followed by multipolar mitosis.

Further, to test whether preventing CPAP-tubulin interaction could impair cancer cell invasiveness, a three-dimensional (3D) organotypic culture model for cancer cells was adapted that recapitulates many aspects of human epithelial cancer tissue architecture. Inducing CPAPΔT in H1975 organoids prevented the formation of actin-positive invasive protrusions that invade the surrounding matrix.

Finally, to explore the effect of CPAPΔT on the growth of MDA-MB-231 cells in vivo, CPAPΔT carrying MDA-MB-231 cells was introduced subcutaneously into nude mice and the tumor growth rate was monitored.

In contrast to control cells, CPAPΔT cells resulted in significant decrease in in vivo growth of breast cancer xenografts accompanied by reduced cell proliferation.

Overall, these results suggest that CPAP-tubulin interaction is a cancer target and preventing CPAP-tubulin interaction causes premature activation of extra-centrosomes to specifically induce cancer cells to undergo mitotic catastrophe and cell death.

EXAMPLE 4

Building on Examples 1 to 3 and by applying AlphaScreen technology, with a further cell-based assay to evaluate centrosome declustering activity, inter alia compound (A) was identified: a compound that prevented the CPAP-tubulin interaction with an $IC_{50}$ value of 0.453 μM and satisfied the screening criteria of declustering centrosomes at 0.5 to 1 μM.

In order to improve biochemical and cellular potency of compound (A), structural activity relationship assisted-medicinal chemistry was performed and compound (A) was modified by replacing the —NH—$CH_2$—$CH_2$—$CH_2$—$CH_3$ group with an —O—$CH_3$ group. Resulting compound (B) inhibited CPAP-tubulin interaction with an $IC_{50}$ value of 0.689 μM and exhibited increased stability and solubility with a potent centrosome declustering activity in cancer cells.

EXAMPLE 5

To evaluate the effect of compound (A) in cancer cells, a spectrum of breast cancer-(BT549, MDA-MB-231), lung cancer-(TKI-sensitive PC9, TKI-resistant $H1975^{T790M}$ or HCC827 with C-met amplification) and hepatocellular carcinoma-(POP10) cells was treated with compound (A) for 24 h.

Strikingly, compound (A) at as low as 500 nM in BT549 cells caused declustering of extra-centrosomes in interphase, with each nucleating massive microtubule asters, indicating that compound (A) prematurely activates interphase centrosomes. As a result, cancer cells failed to cluster their extra-centrosomes instead exhibiting multipolar spindles both in interphase and mitosis. Live cell experiments with MDA-MB-231 cells expressing tubulin-GFP further revealed that similar to CPAPΔT transfected cells, compound-(A)-treatment also caused prolonged mitosis with eventual apoptosis. Accordingly, compound (A) effectively prevented cancer cell proliferation with $IC_{50}$ values between 0.86 μM and 2.9 μM. The 24 h pulse labeling experiment-using ethynyl-deoxyuridine (EdU) further supported this finding revealing a reduced number of compound-(A)-treated cancer cells with EdU incorporation, indicating that fewer cells have entered S-phase. Taken together, these data show that compound-(A)-mediated premature activation of extra centrosomes causes multipolar mitosis, mitotic catastrophe to effectively impair the proliferation of cancer cells.

EXAMPLE 6

Although tubulin binders have been shown to possess excellent anticancer activity, their usage is limited due to their non-selective activity in normal cells. Since compound (A) is a tubulin binder, its tolerability and cellular toxicity in comparison to taxol in Plk-4-inducible MCF10A was evaluated. Taxol, at 100 nM concentration itself non-selectively prevented MCF10A cells proliferation regardless of whether they carry extra centrosomes or not. In addition, taxol treatment did not affect centrosome clustering but instead collapsed the spindles by stabilizing microtubules.

In contrast, compound-(A)-treatment specifically inhibited the proliferation of MCF10A cells that harbor extra centrosomes via its centrosome declustering activity.

Importantly, MCF10A cells with two centrosomes could tolerate compound (A) up to 10 μM without displaying any defect in their bipolar mitotic spindles indicating that compound (A) does not affect microtubule dynamics in normal cells.

EXAMPLE 7

A cell proliferation experiment using erlotinib, a known EGFR TKI inhibitor, revealed that both H827 and A549 cells responded to erlotinib relatively at higher concentration with an $IC_{50}$ value of 6.9 µM and 5 µM, respectively. These results indicate that H827 and A549 cells are to some extent resistant to erlotinib as described previously. Analyses of centrosomes revealed that erlotinib treatment does not affect centrosome clustering in H827.

However, the EGFR inhibitor erlotinib was more potent in preventing the proliferation of H827 when combined with 750 nM (half of its original $IC_{50}$) of compound (A). Combinatorial treatment with compound (A) decreasing the IC50 value of erlotinib from 6.9 µM to 30 nM suggests that compound (A) could synergize H827 cells to erlotinib. Similarly, addition of 1.5 µM of compound (A) to A549 cells reduced the $IC_{50}$ value of erlotinib from 5.07 µM to 0.5 µM.

Finally, combination (compound (A) plus erlotinib) but not single agent (erotinib) alone effectively prevented the formation of invasive protrusions from the threedimensional (3D) organotypic cultures of H1975 and A549.

EXAMPLE 8

To evaluate the anti-tumor activity of compound (A), compound (A) was delivered to nude mice bearing subcutaneous human prostate tumor cell (PC3) xenografts. Compound (A) was administered (10 mg/kg) by oral gavage once per day and the rate of tumor growth was monitored. Compared to vehicle treated controls, it was noticed a reduction in tumor growth rate in compound-(A)-treated mice. Importantly, the anti-tumor activity of compound (A) could be observed as determined by reduced tumor volume with respect to control at day 10.

EXAMPLE 9

Figure 1:
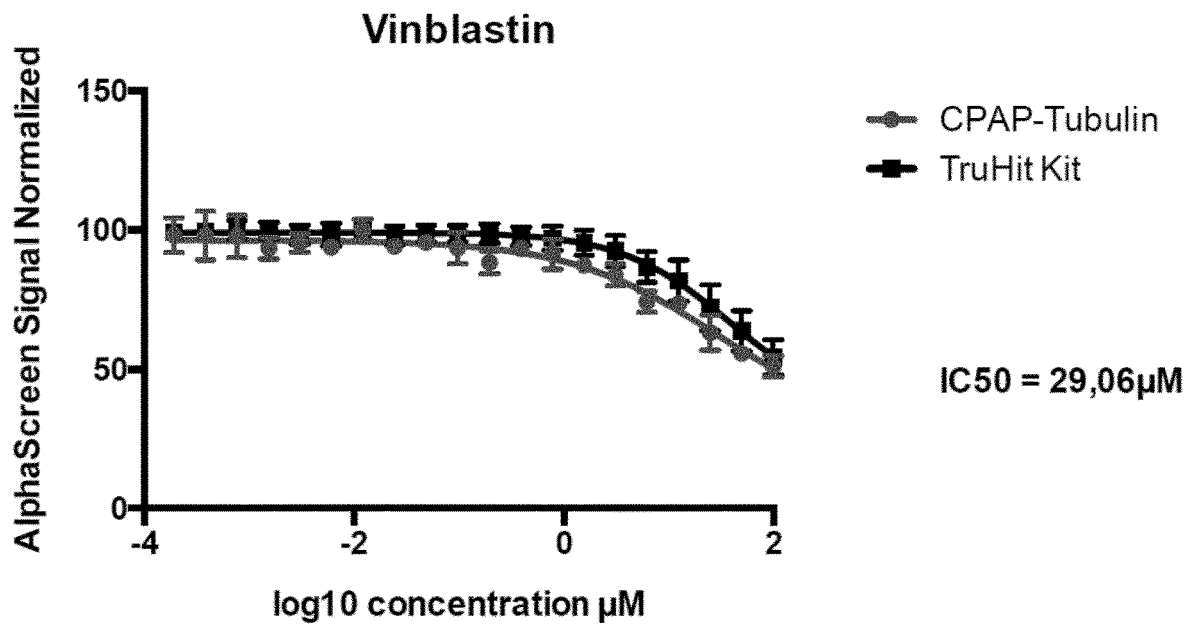
FIGS. 1 to 4, 19 and 20 show normalized AlphaScreen signal for conventional tubulin binders Vinblastin (FIG. 1), Paclitaxel (FIG. 2), Docetaxel (FIG. 3) Colchicin (FIG. 4), Bactallin III (FIG. 19) and Taxol (FIG. 20).
Figure 2:
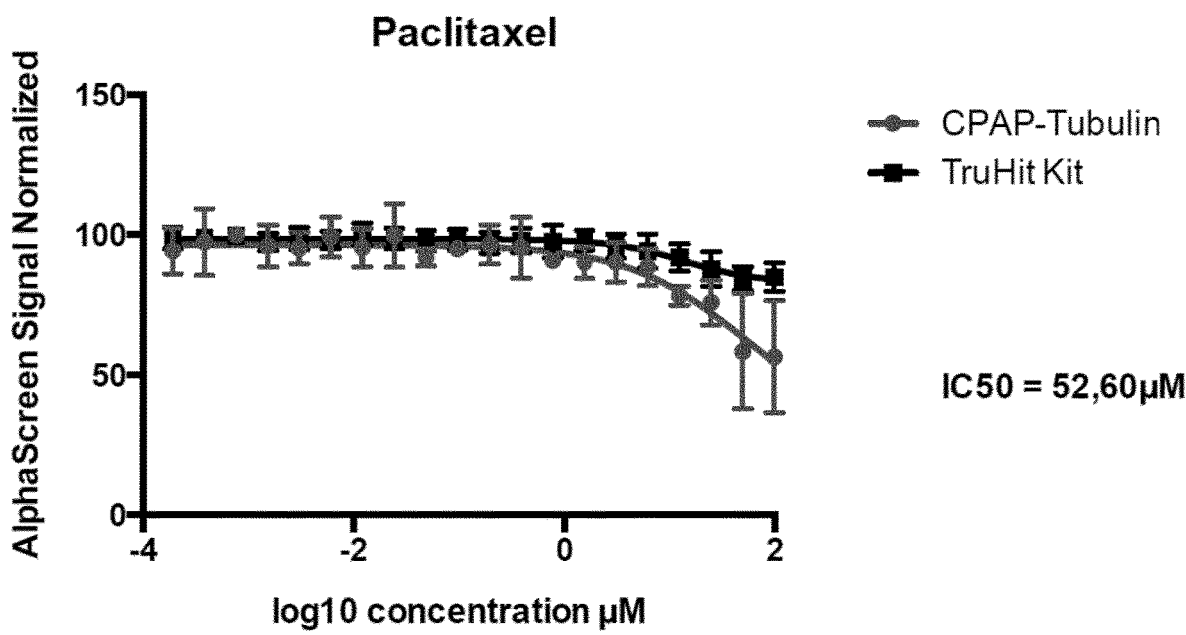
Figure 3:
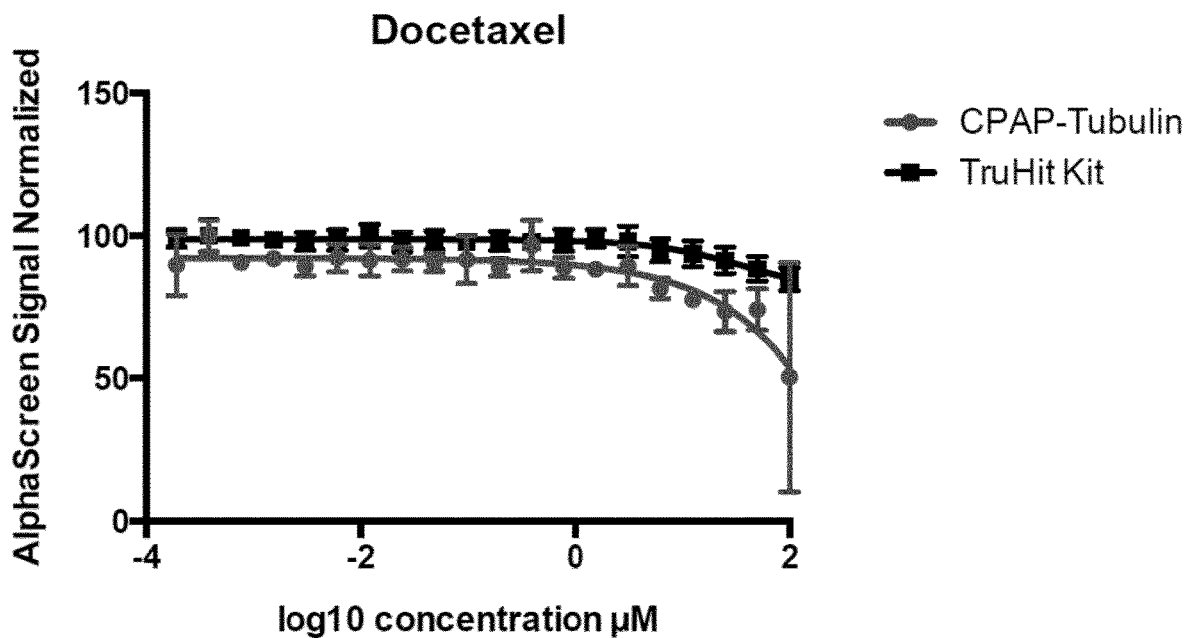
Figure 4:
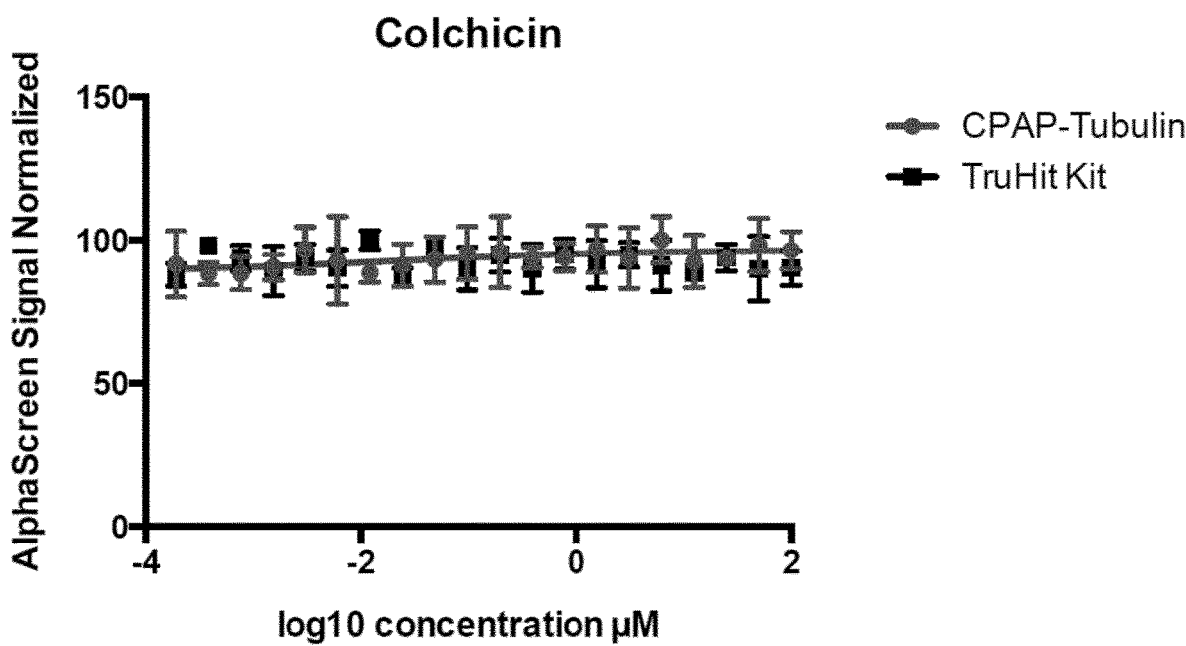
Figure 5:
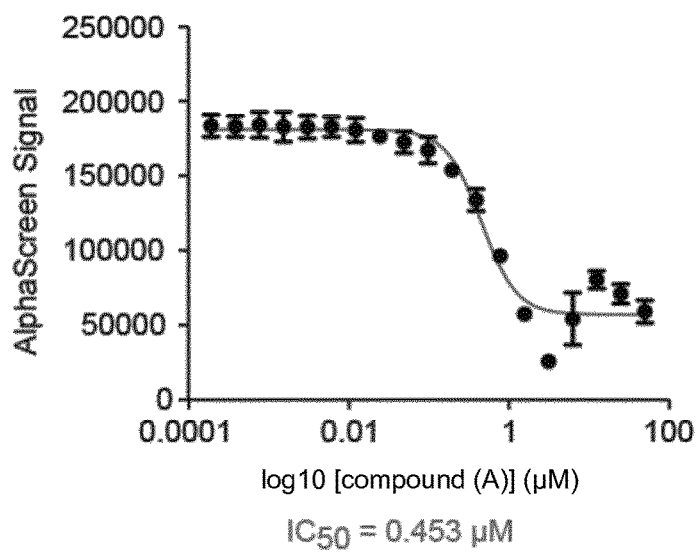
FIGS. 5 to 16 show normalized AlphaScreen signal for the inventive compounds (B) to (L).
Figure 6:
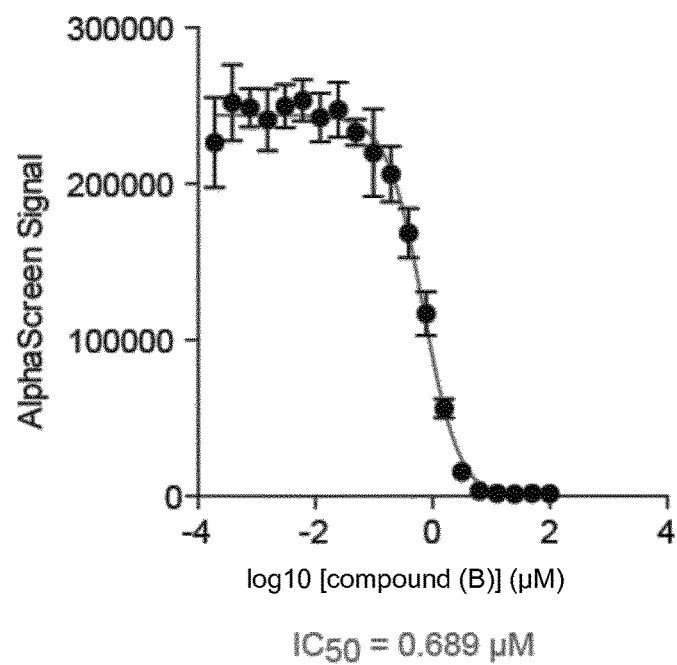
Figure 7:
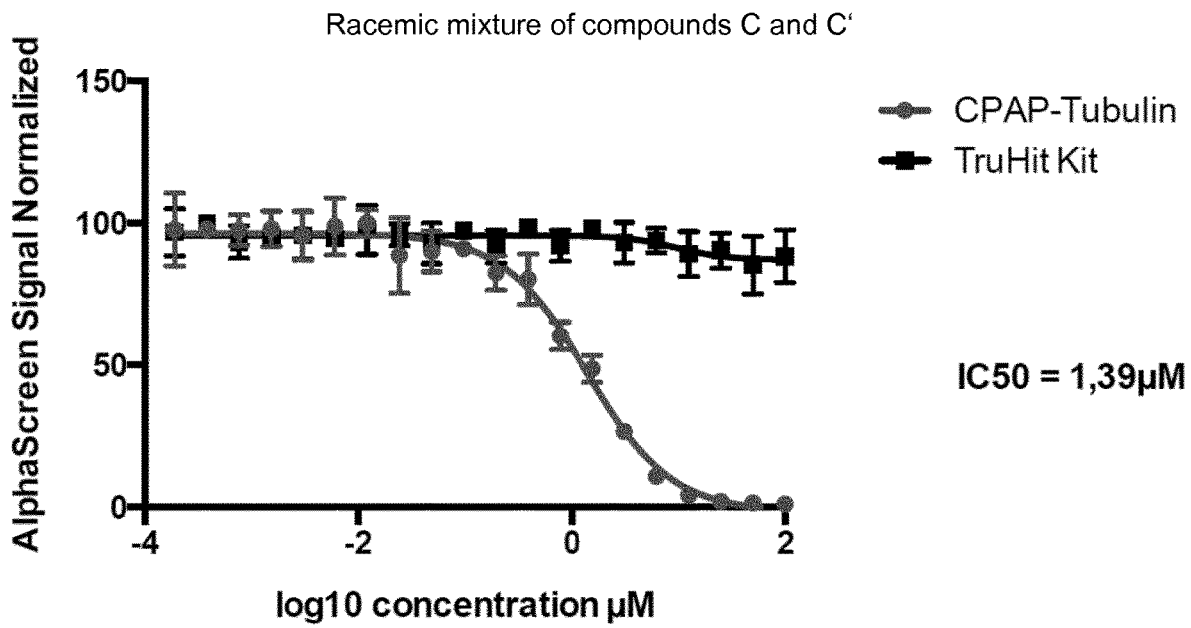
Figure 8:
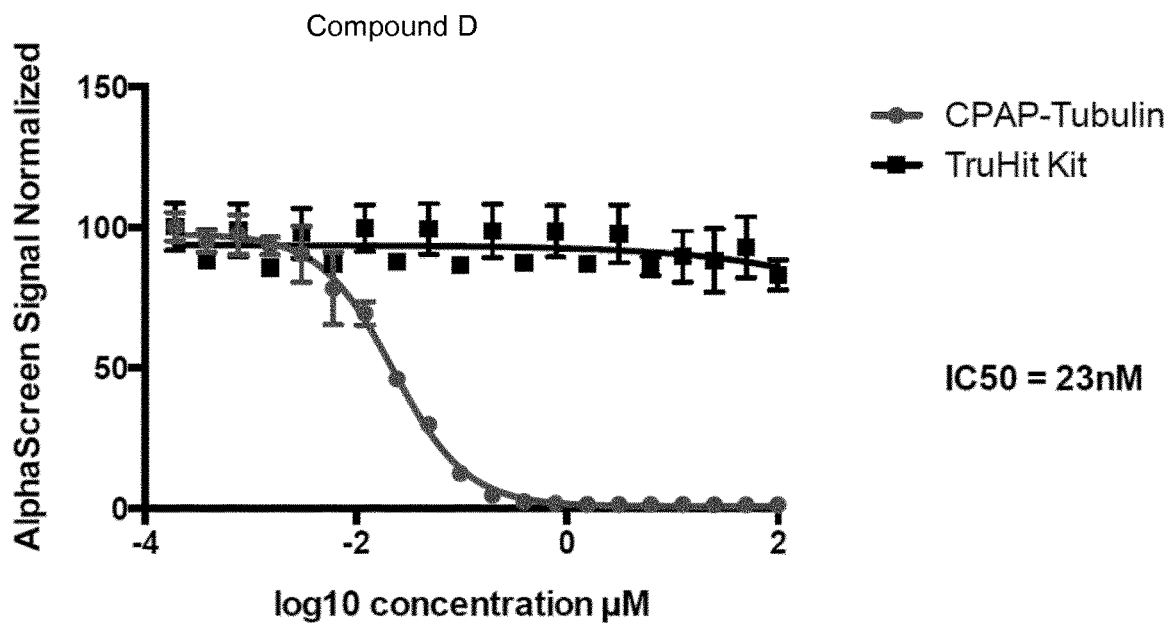
Figure 9:
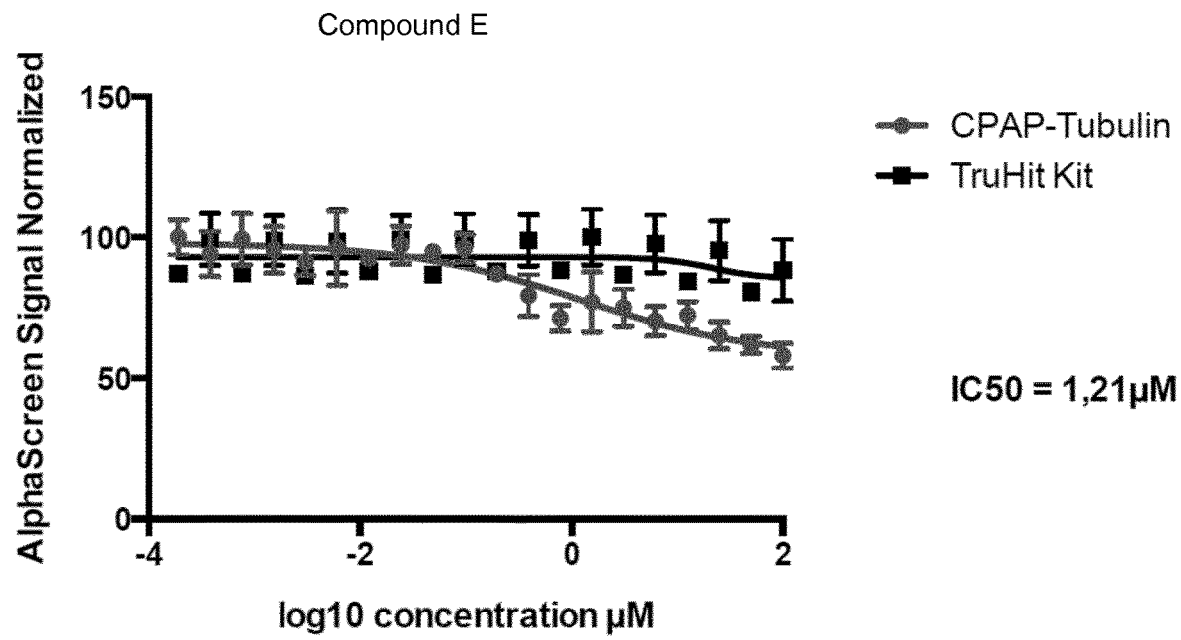
Figure 10:
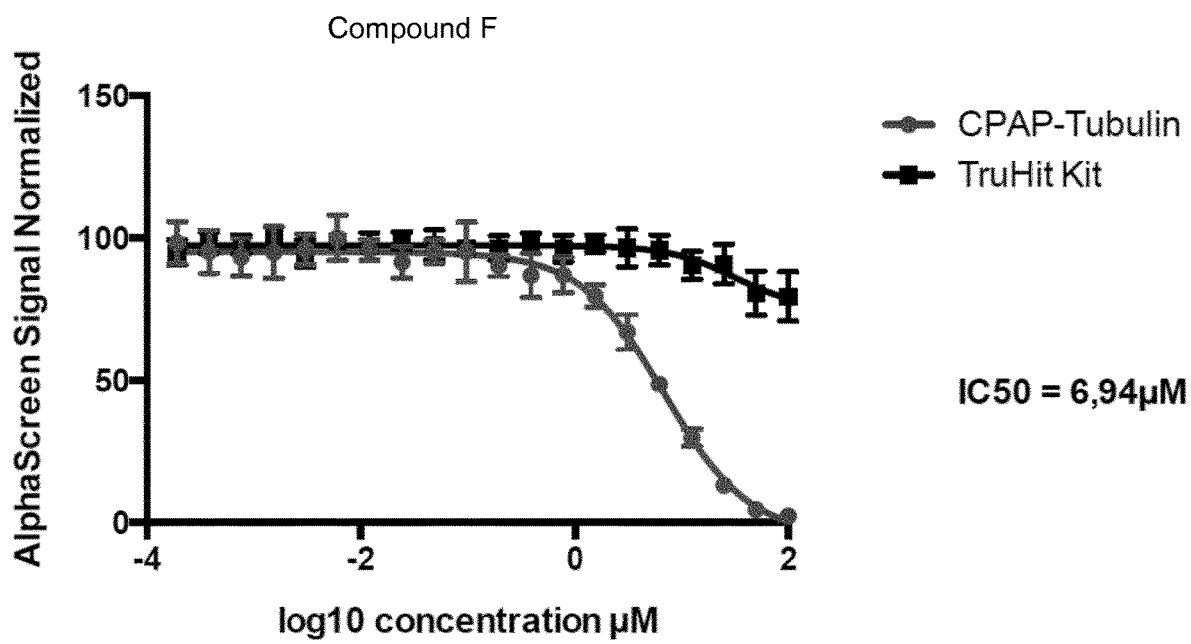
Figure 11:
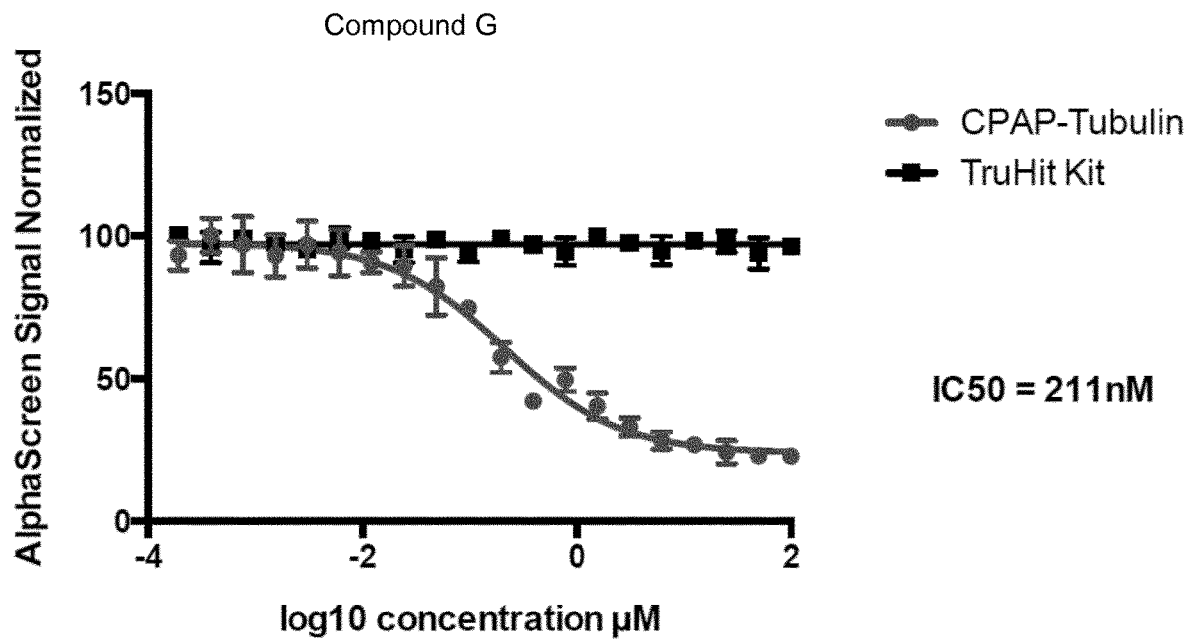
Figure 12:
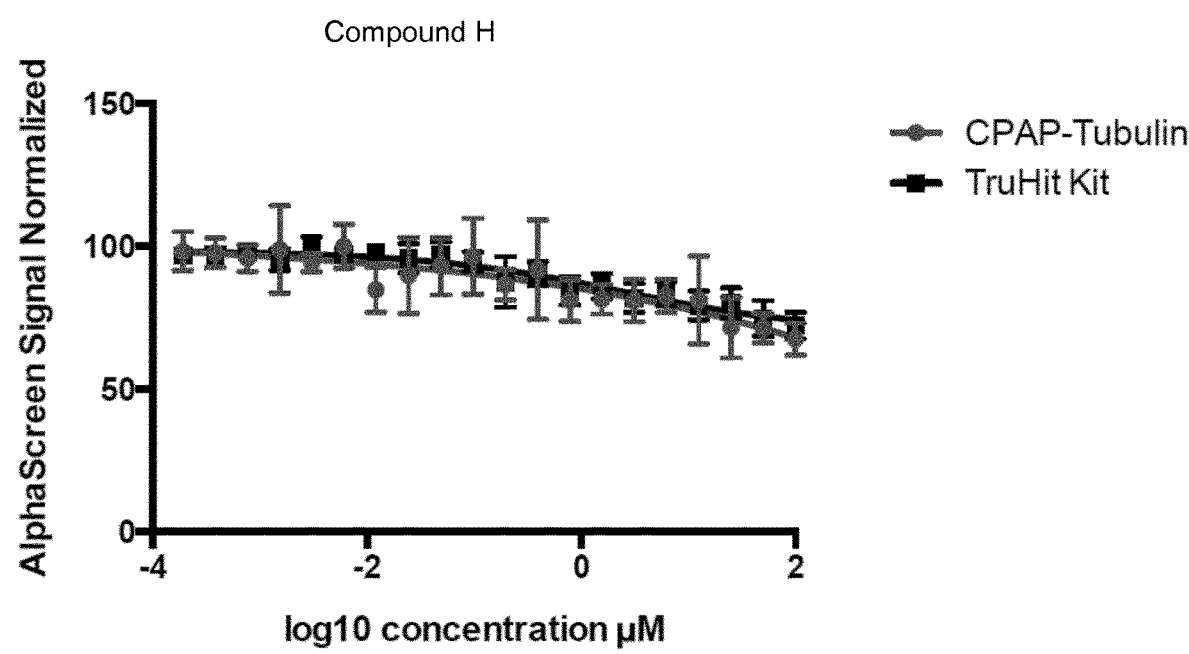
Figure 13:
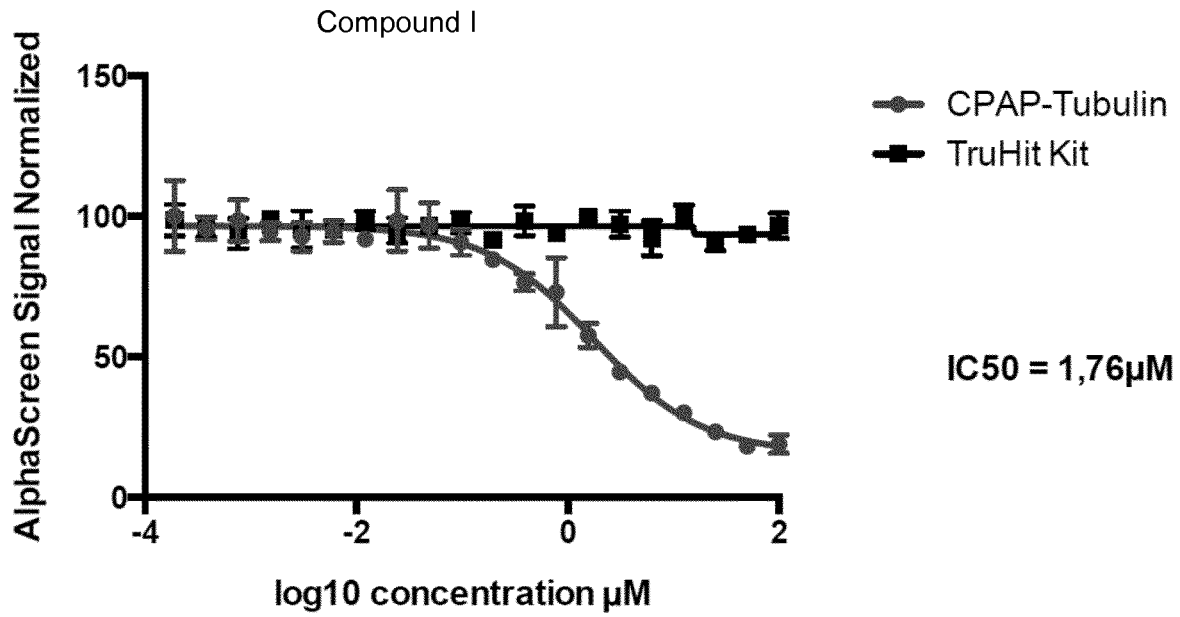
Figure 14:
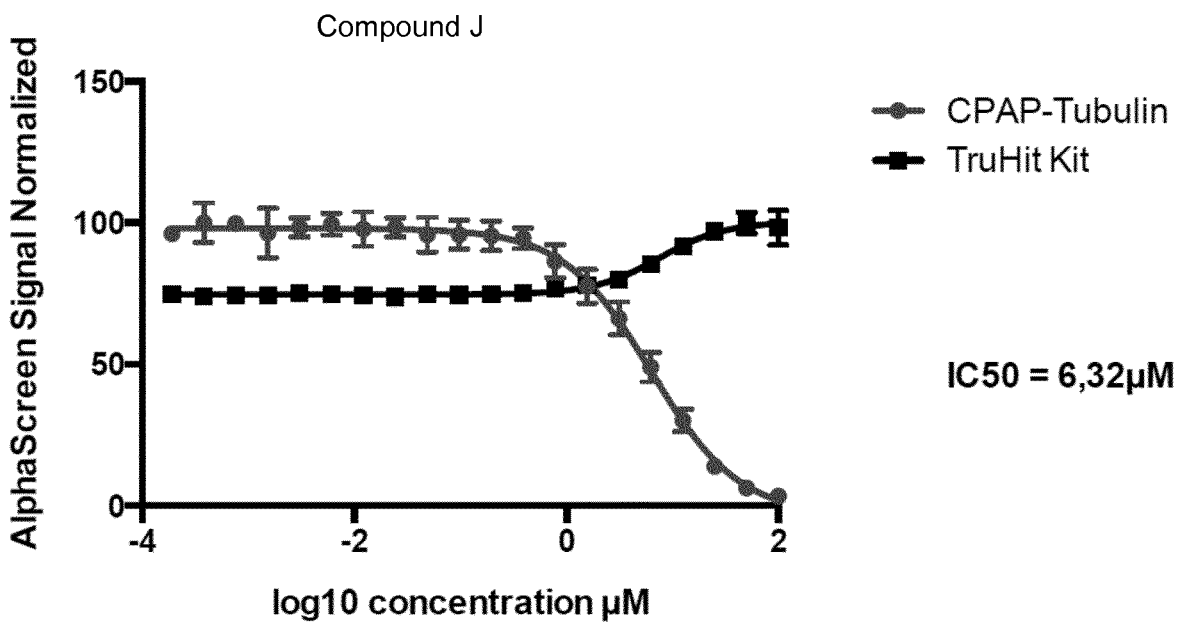
Figure 15:
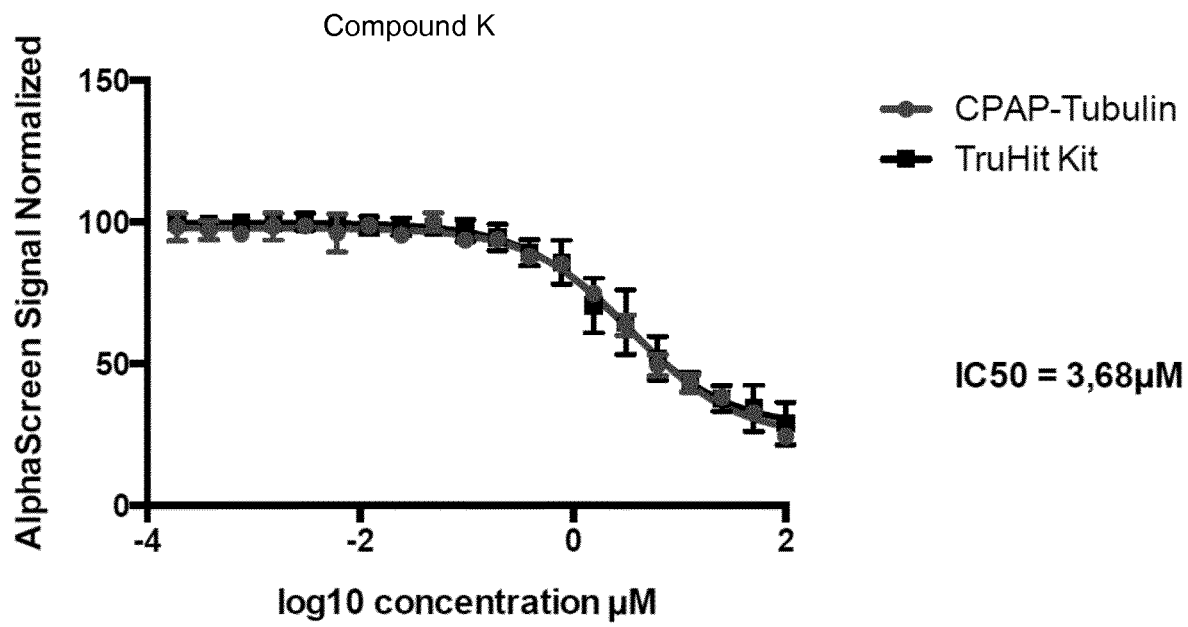
Figure 16:
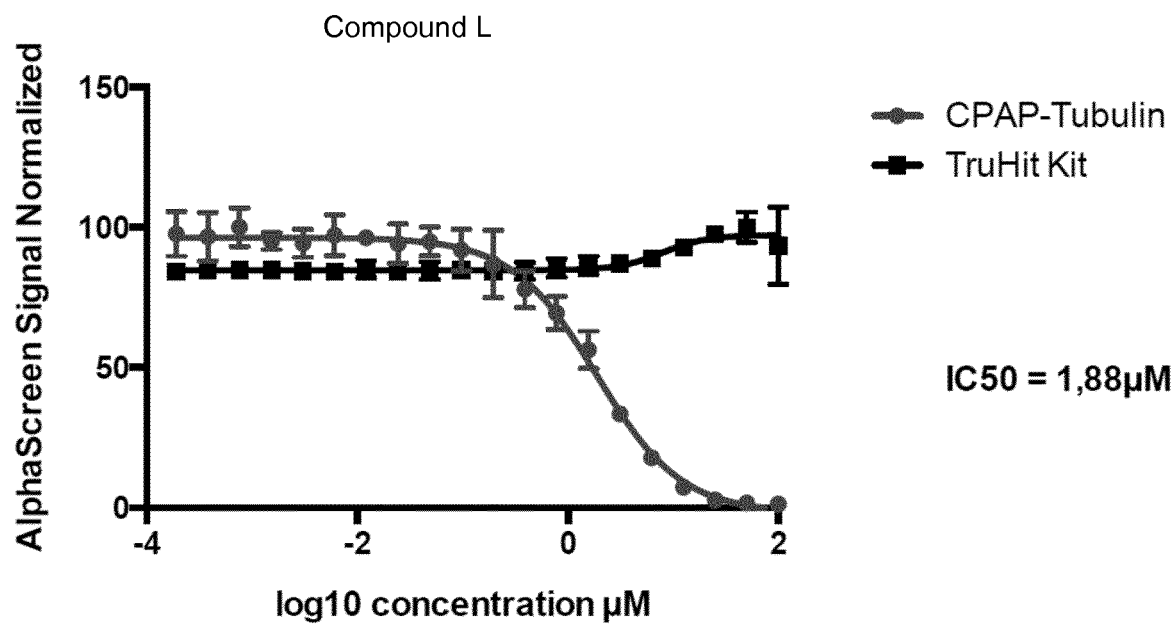
Figure 17:
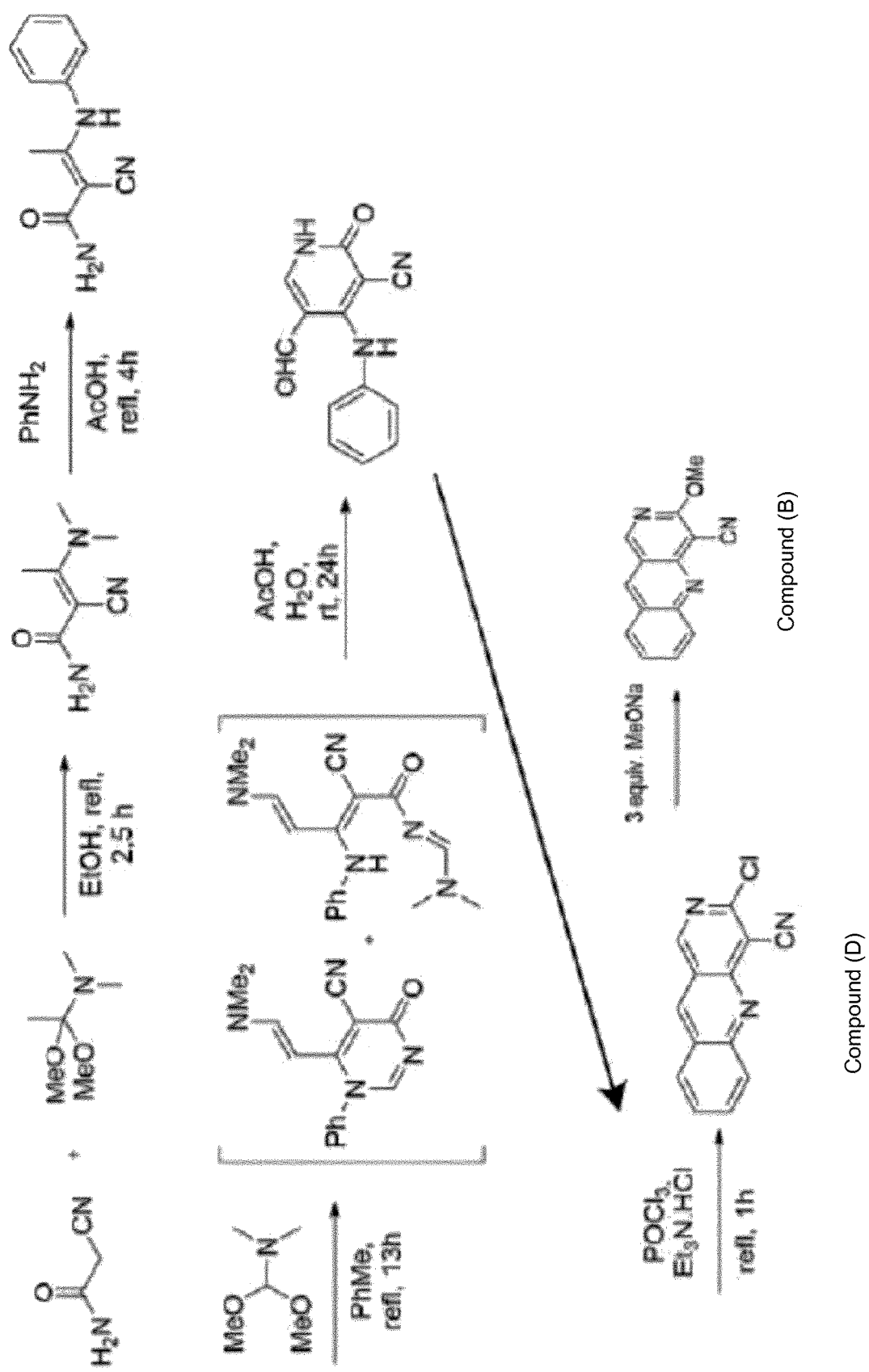
FIG. 17 shows the synthesis scheme for compound (B).

Compound (B) was synthesized according to the scheme provided with FIG. 17. The educt 3-Chlorobenzo[b][1,6]naphthyridine-4-carbonitrile was synthesized as described in Russ. Chem. Bull., Int. Ed. 2002, 51, 2121-2128, Chem. Heterocycl. Compd. 1986, 22, 909-914, Russ. Chem. Bull., Int. Ed. 2004, 873-881.

Compound (B) (3-Methoxybenzo[b][1,6]naphthyridine-4-carbonitrile) was prepared from Chlorobenzo[b][1,6]naphthyridine-4-carbonitrile according to the following procedure: A suspension of 3-Chlorobenzo[b][1,6]naphthyridine-4-carbonitrile (400 mg, 1.67 mmol) in a mixture of absolute methanol (30 mL) and dry tetrahydrofuran (20 mL) was stirred at reflux and 0.5 M solution of sodium methoxide in methanol (4.00 mL, 2.00 mmol, 1.2 eq) was added dropwise over 1 h. The resulting brown solution was kept at reflux for further 30 min, cooled, quenched with saturated aqueous solution of ammonium chloride (2 mL) and concentrated in vacuo. The residue was partitioned between water (10 mL) and methylene chloride (50 mL). The layers were separated and the aqueous phase was extracted with methylene chloride (2×15 mL). The combined organic extract was washed with saturated aqueous ammonium chloride, dried over anhydrous sodium sulfate, filtered and concentrated in vacuo. The residue was subjected to reverse-phase flash chromatography (gradient: 0 to 45% acetonitrile in water v/v) to provide the title compound (210 mg, 0.89 mmol, 54%) as a yellow solid.

NMR spectra were recorded at 303 K on a Broker Avance III HD 400 (400 MHz) spectrometer. Chemical shifts are reported in parts per million (ppm) relative to residual d5-DMSO (δH=2.50 ppm) and d6-DMSO (δC=39.52 ppm). Splitting patterns are designated as s (singlet), d (doublet), t (triplet), td (triplet of doublets), ddd (doublet of doublets of doublets), m (multiplet) or bs (broad signal). The coupling constants (J) are reported in Hertz (Hz).

TLC (pentane: ethyl acetate, 2:1 v/v): Rf=0.33; 1H NMR (400 MHz, d6-DMSO) δ 9.71 (s, 1H, H-1), 9.48 (s, 1H, H-10), 8.26 (d, J=8.4 Hz, 1H, H-9), 8.15 (d, J=8.8 Hz, 1H, H-6), 8.04 (ddd, J=8.6, 6.6, 1.5 Hz, 1H, H-7), 7.70 (td, J=6.8, 3.3 Hz, 1H, H-8), 4.23 (s, 3H, OCH3); 13C NMR (101 MHz, d6-DMSO) δ 166.6 (C-3), 160.4 (C-1), 152.6 (C-9a), 150.0 (C-10a), 141.5 (C-10), 135.2 (C-7), 130.5 (C-9), 128.8 (C-6), 126.8 (C-8), 126.3 (C-4a), 118.3 (C-5a), 115.2 (CN), 86.5 (C-4), 56.1 (OCH3).

IR (ATR) vmax (cm-1) 3044, 3019, 2958, 2894, 2847, 2224, 1605, 1557, 1512, 1466, 1411, 1331, 1285, 1181, 1140, 1107, 1041, 969, 800, 741, 613.

ESI-H RMS (m/z): [M+H]+ calcd. For C14H10N3O, 236.08184; found, 236.08194; LCMS (m/z): [M+H]+236, retention time 3.23 min.

EXAMPLE 10

The effects of compound (B) on a spectrum of breast cancer-(BT549, MDA-MB-231),NSCLC-(PC9, TM-resistant H1975T790M, HCC827-GR) and hepatocellular-carcinoma-(POP10)-cells were tested by treatment with compound (B) for 72 hrs.

Compound (B) prevented cancer cell proliferation with IC50 values between 0.86-2.9 µM. Analyzing centrosomes revealed that compound (B) prevented clustering of extra centrosomes during interphase, with each nucleating enhanced microtubule asters, suggesting that compound (B) prematurely activates extra centrosomes in interphase resulting in the formation of multipolar spindles in interphase and mitosis.

Live imaging of compound (B)-treated MCF10A (+Dox, extra centrosomes) and HCC827-GR cells revealed that similar to CPAPΔT expression, compound (B)-treatment caused extra centrosomes to nucleate enhanced microtubule asters at interphase itself. Compound (B)-induced microtubule asters persisted in cells, preventing extra centrosomes from clustering, causing multipolar spindles and prolonged mitosis with an apparent apoptosis.

Together, these results suggest that compound (B)-treatment can impair proliferation of extra centrosome containing cells.

EXAMPLE 11

Mechanisms by which compound (B) activates extra centrosomes to nucleate enhanced microtubules were identified. Peri-centriolar material (PCM) recruitment to centrosomes is required for microtubule nucleation. Compound (B)-treated interphase centrosomes prematurely nucleating microtubules suggest that these centrosomes recruit enhanced levels of PCM.

Figure 18:
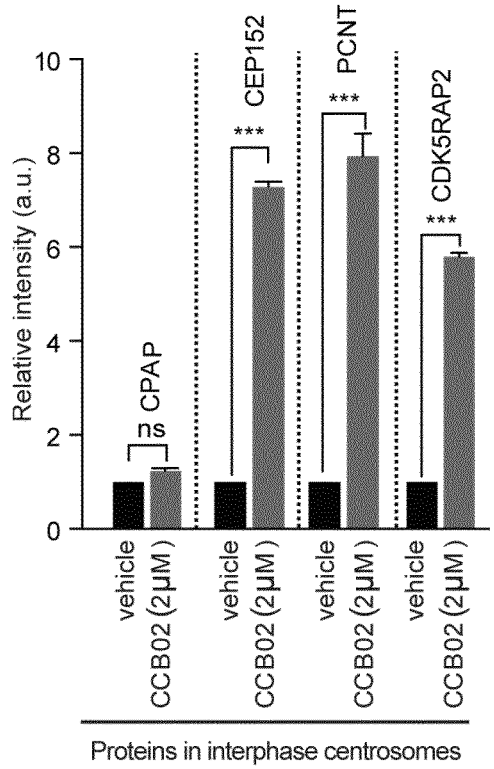
FIG. 18 shows proteins in interphase centrosomes.
Figure 19:
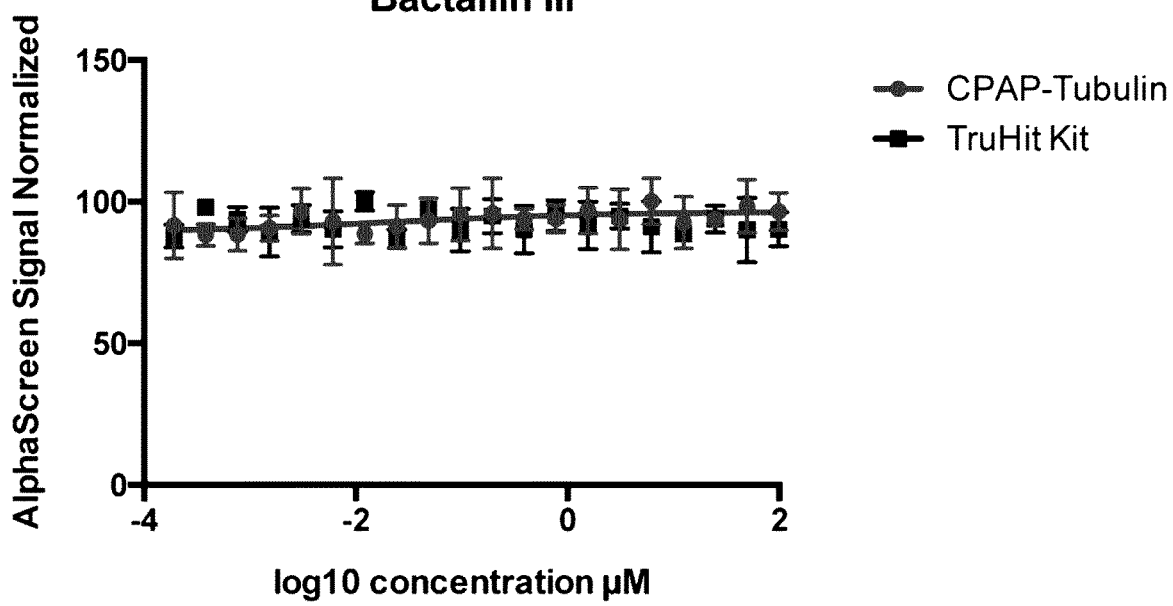
Figure 20:
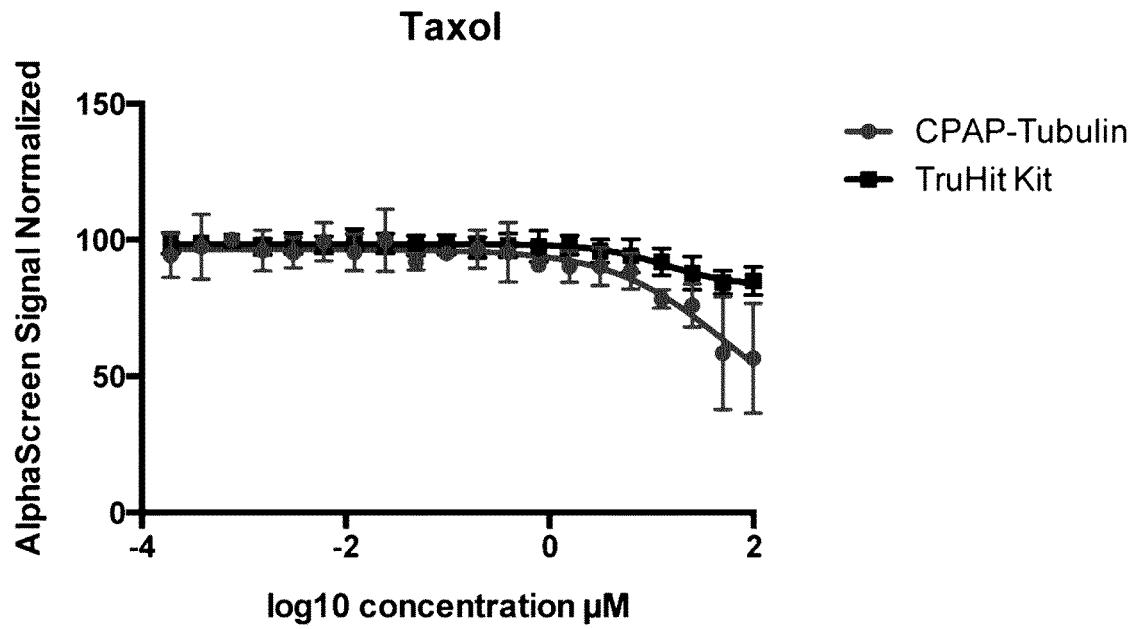

To test this, we estimated the amounts of Cep152, PCNT and CDK5RAP2 recruitment to interphase centrosomes of compound (B)—treated MCF10A cells. Notably, both human and Drosophila CPAP interacts with these proteins to form the S-CAP complex. High-resolution imaging and heat map intensity analyses revealed that interphase centrosomes recruit enhanced amounts of these proteins as compared to vehicle-treated cells (FIG. 18). As a result, compound (B)-treated interphase centrosomes display enhanced microtubule nucleation suggesting that compound (B) could activate centrosomes.

This finding is in agreement with live imaging experiments where compound (B) treated cells display centrosomes with robust microtubule nucleation.

Furthermore, western blot analysis of biochemically fractionated centrosomes revealed that-treated cells contained centrosomes with elevated levels of CPAP-interacting proteins.

Finally, it was tested if compound (B) could prevent CPAP-tubulin interaction in cells and simultaneously enhance the ability of CPAP to bind its interacting proteins. CPAP complexes from cytoplasmic extracts of compound (B)-treated MCF10A cells were immunopurified. It was identified that compound (B) specifically perturbs CPAP-tubulin interaction thereby allowing CPAP to bind an enhanced amount of its interacting proteins.

Together, these results suggest that chemical inhibition of the CPAP-tubulin interaction could enhance the recruitment of CPAP interacting proteins to centrosomes.

EXAMPLE 12

Most tubulin-binding agents act on spindle microtubules and thus prevent mitosis nonspecifically. To evaluate if the effects of compound (B) are specific to CPAP-tubulin interaction and not due to general effects on microtubule dynamics, compound (B) was compared to known tubulin binders such as Taxol, Bactallin III, Docetaxel and Vinblastine (FIGS. 1, 3, 19, 20).

Except compound (B), neither of the tested tubulin binders could perturb CPAP-tubulin interaction, enhance PCM recruitment to interphase centrosomes and prevent extra centrosomes from clustering. Notably, disrupted mitotic spindles in cells treated with tubulin binding agents were observed and this could be due to their general toxicity to microtubules. In addition, to rule out the possible microtubule toxic effect of compound (B), live imaging experiments were performed. It was found that compound (B) up to 5 µM does not affect microtubule dynamics, cell cycle progression or mitotic spindle assembly of two-centrosomes containing cells. Furthermore, in contrast to taxol, which at 30 nM itself collapsed the spindles of two-centrosomes containing cells, compound (B) up to 8 µM did not prevent the formation of bipolar mitotic spindles.

These results suggest that the anti-proliferative effects of compound (B) are not due to altering microtubule dynamics.

EXAMPLE 13

Centrosome amplification triggers cellular invasion in 3D cultures 8. To test if compound (B)-mediated effects could impair the invasive behavior of cancer cells, 3D-organotypic cultures of H1975T790M, HCC827-GR and A549 (KRASG12S) exhibiting resistance to EGFR-TKIs were used.

Figure 21:
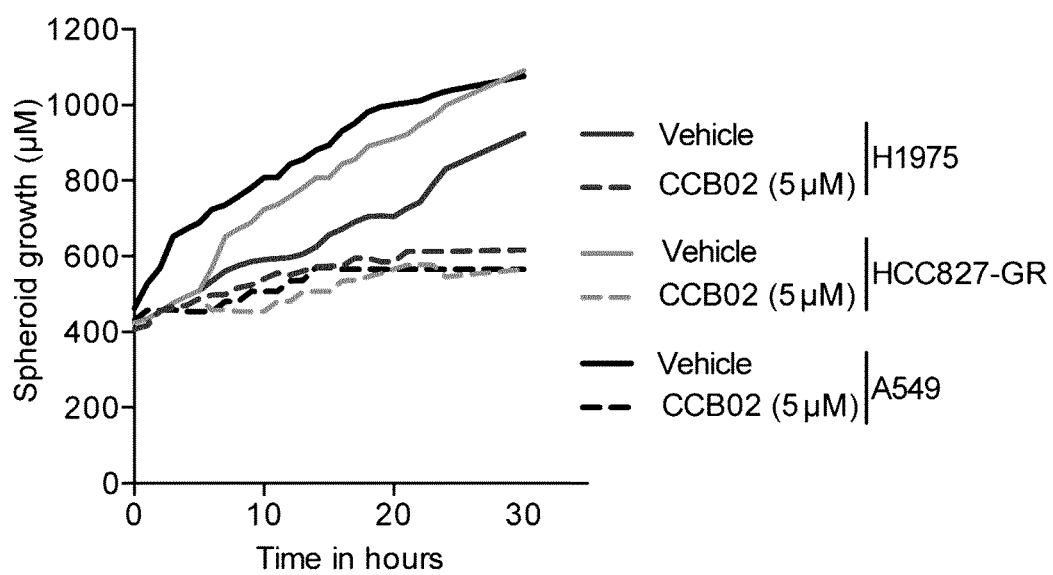
FIG. 21 shows the growth of activated caspase-positive cells in H1975T790M organoids treated with compound (B)

In contrast to 5 µM erlotinib treatment, a known TM, compound (B) at 5 µM was sufficient to prevent actinpositive invasive protrusions emerging from 3D spheres. Instead, compound (B)-treatment caused cell-rounding, characteristics of prolonged mitotic arrest with concomitant cell death as revealed by activated caspase-positive cells in H1975T790M organoids. As a result, compound (B)-treated organoids did not grow further from its original size (FIG. 21).

Together, these data show that compound (B) could impair NSCLC cells invasive behavior in vitro.

EXAMPLE 14

To evaluate if compound (B) has anti-tumor activity in vivo, nude mice bearing subcutaneous human prostate (PC3) and breast (MDA-MB-231) tumor xenografts were used.

In each case, two groups of mice bearing tumor volume >100 mm$^3$ were used. Compound (B) (10 or 20 mg, Kg-1/day) by oral gavage was delivered. At the end of treatment, we measured the total tumor volume of compound (B)-treated groups and compared with vehicle-treated controls. A significant reduction in tumor growth rate in compound (B)-treated mice was noticed.

Importantly, the body weights of treated animals did not change. This finding suggests that compound (B) has anti-tumor activity with less or no adverse effects.

The anti-tumor activity of compound (B) resulted in reduced tumor volume with respect to control after 10 (for PC3) and 31 (for MDA-MB-231) days (FIGS. 22 and 23).

EXAMPLE 15

TKI (tyrosine kinase inhibitor) resistant lung cancer cell lines (A549, HCC827-GR and H1975) were treated with Erlotinib and compound (B).

Dose-response curves to show the effect of single-agent TKI in the presence or absence of compound (B) in HCC827-GR cells (FIG. 24). For A549G12S cells, single-agent TKI in the presence of compound (B) and in the absence of (FIG. 25). 1 µM of compound (B) is used for 72-96 hours. Error bars, mean±SEM.

A summary of IC50 values of TKI resistant (NSCLC) lung cancer cell lines is given in FIG. 26. Error bars, mean±SEM. Values are from three independent experiments. Unpaired t-test *P<0.01, **P<0.001.

EXAMPLE 16

Compound (M) was synthesized according to the scheme provided with FIG. 27.

Compound (M) was synthesized according to the following procedure: Under an argon atmosphere, to a solution of 300 mg 3-Chlorobenzo[b][1,6]naphtiridine-4-carbonitrile (1.25 mmol, 1 eq.) in 4 mL d6-DMSO were added 231 mg Glycine tert-butyl ester hydrochloride (1.38 mmol, 1.1 eq.), 79.5 mg (0.75 mmol, 0.6 eq.) Na2CO3, and 72.6 mg (1.25 mmol, 1 eq.) KF. The reaction mixture was then heated in a microwave (125° C., 300 W, 9 bar) for 1 hour. To the black solution was then added 2 mL water and the aqueous phase was extracted with CH2Cl2 (4×50 mL). The combined organic phases were dried over MgSO4, and after filtration, the solvent was removed under reduced pressure. The residue was purified by flash column chromatography on silica (CH2Cl2:EtOAc=3:1) to afford 106 mg (0.31 mmol, 25%) of a dark orange solid. To a solution of 71 mg (0.21 mmol, 1 eq.) tert-butyl ester derivative in 2 mL CH2Cl2 was added 2 mL (0.03 mmol, 0.2 eq.) TFA at 0° C. The reaction mixture was then stirred at room temperature for 1 hour. The solvent was removed in vacuo and the obtained solid was washed with a small amount of CH2Cl2 to obtain the desired product in 57 mg (0.21 mmol, 98%) yield as a orange solid.

The Error bars in FIGS. 1 to 16, 19 and 20 indicate data from a triplicate determination. The TruHit Kit captures possible effects on AlphaScreen assay technology. The experimental data of FIGS. 1 to 4, 19 and 20 shows that the compounds according to the invention exhibited a dose dependent reduction of CPAP-tubulin interaction, whereas the conventional tubulin binders did not show any reduction in the signal. This indicates that CPAP-tubulin interaction is specific for the compounds according to the invention.

The invention claimed is:

1. A method comprising:
   administering to a patient in need thereof a lung cancer, breast cancer, liver cancer or prostate cancer treating effective amount of a compound of the general formula (1)

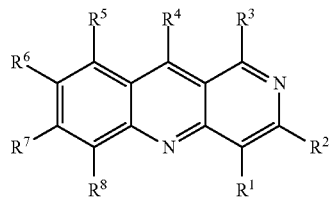

(1)

or a physiologically acceptable salt thereof;
wherein
$R^1$ represents —CN;
$R^2$ represents —F, —Cl, —Br, —I, —O—$C_{1-8}$—alkyl, —S—phenyl, —S—$C_{1-8}$—alkyl—C(=O)NH—phenyl, —NH—$C_{1-8}$—alkyl, —NH—$C_{1-8}$—alkyl—$CO_2H$, —NH—$C_{1-8}$—alkyl—phenyl or —$C_{3-12}$—cycloalkyl or $R^2$ represents $NR^AR^B$, wherein $R^A$ and $R^B$ together with the nitrogen atom to which they are attached form a ring and mean —$(CH_2)_{2-6}$;
or
$R^1$ and $R^2$ jointly form a five- or six-membered ring, the ring atoms of which respectively independently of one another are C, S or O, wherein the ring is aromatic or non-aromatic, unsubstituted or mono- or polysubstituted by substituents selected independently of one another from the group consisting of —F, —Cl, —Br, —I, —CN, —$NO_2$, —CHO, -$R^Z$, —C(=O)$R^Z$, —C(=O)H, —C(=O)OH, —C(=O)$OR^Z$, —C(=O)$NH_2$, —C(=O)$NHR^Z$, —C(=O)$N(R^Z)_2$, —OH, —$OR_Z$, —OC(=O)H, —OC(=O)$R^Z$, —OC(=O)—$OR^Z$, —OC(=O)—$OR^Z$, —OC(=O)$NHR^Z)_2$, —SH, —$SR^Z$, —$SO_3H$, —S(=O)$_{1-2}$—$R^Z$, —S(=O)$_{1-2}NH_2$, —$NH_2$, —$NHR^Z$, —N($R^Z$)$_2$, —$N^+(R^Z)_3$, —$N^+(R^Z)_2O^-$, —NHC(=O)$R^Z$, —NHC(=O)$OR^Z$, —NHC(=O)$NH_2$, —NHC(=O)$NHR^Z$, —NHC(=O)—N($R^Z$)$_2$, —Si($R^Z$)$_3$ and —PO(O$R^Z$)$_2$ and wherein when $R^1$ and $R^2$ form a six-membered ring, the ring comprises at least one S or O;
$R^3$, $R^4$, $R^5$, $R^6$, $R^7$ and $R^8$, independently of one another, represent —H, —F, —Cl, —Br, —I, —CN or —$C_{1-8}$-alkyl;
wherein in each case $R^z$, respectively independently, means —$C_{1-8}$-aliphatic, —$C_{3-12}$-cycloaliphatic, -aryl, heteroaryl, —$C_{1-8}$-aliphatic—$C_{3-12}$-cycloaliphatic, —$C_{1-8}$-aliphatic-aryl, —$C_{1-8}$-aliphatic-heteroaryl, —$C_{3-8}$-cycloaliphatic—$C_{1-8}$-aliphatic, —$C_{3-8}$-cycloaliphatic-aryl or —$C_{3-8}$-cycloaliphatic-heteroaryl;
wherein in each case "aliphatic", respectively independently, means a branched or unbranched, saturated or a mono- or polyunsaturated, unsubstituted or mono- or polysubstituted, aliphatic hydrocarbon residue;
wherein in each case "cycloaliphatic", respectively independently, means a saturated or a mono- or polyunsaturated, unsubstituted or mono- or polysubstituted, alicyclic, mono- or multicyclic hydrocarbon residue;
wherein in each case with respect to "aliphatic" and "cycloaliphatic", "mono- or polysubstituted", respectively independently, means the mono- or polysubstitution of one or more hydrogen atoms by —F, —Cl, —Br, —I, —CN, —$NO_2$, —CHO, =O, —$R^z$, —C(=O)$R^z$, —C(=O)H, —C(=O)OH, —C(=O)$OR^z$, —C(=O)$NH_2$, —C(=O)$NHR^z$, —C(=O)N($R^z$)$_2$, —$OR^z$, —OC(=O)H, —OC(=O)$R^z$, —OC(=O)—$OR^z$, —(=O)$NHR^z$, —OC(=O)N($R^z$)$_2$, —SH, —$SR^z$, —$SO_3H$, —S(=O)$_{1-2}$—$R^z$, —S(=O)$_{1-2}$$NH_2$, —$NH_2$, —$NHR^z$, —N($R^z$)$_2$, —$N^+(R^z)_3$, —$N^+(R^z)_2O^-$, —NHC(=O)$R^z$, —NHC(=O)$OR^z$, —NHC(=O)$NH_2$, —NHC(=O)$NHR^z$, —NHC(=O)—N($R^z$)$_2$, —Si($R^z$)$_3$ or —PO(O$R^z$)$_2$;
wherein in each case "aryl", respectively independently, means a carbocyclic ring system with at least one aromatic ring, but without heteroatoms in this ring, wherein, if necessary, the aryl residues can be condensed with further saturated, (partially) unsaturated or aromatic ring systems, and each aryl residue can be present in unsubstituted or mono- or polysubstituted form, wherein the aryl substituents can be the same or different and in any desired and possible position of the aryl;
wherein in each case "heteroaryl", respectively independently, means a 5-, 6- or 7-membered cyclic aromatic residue, which contains 1, 2, 3, 4 or 5 heteroatoms, wherein the heteroatoms, the same or different, are nitrogen, oxygen or sulphur, and the heterocycle can be unsubstituted or mono- or polysubstituted; wherein in the case of the substitution on the heterocycle the substituents can be the same or different and can be in any desired and possible position of the heteroaryl; and wherein the heterocycle can also be part of a bi- or polycyclic system;
wherein in each case with respect to "aryl" and "heteroaryl", "mono- or polysubstituted", respectively independently, means the mono- or polysubstitution of one or more hydrogen atoms of the ring system by substituents selected from the group comprising —F, —Cl, —Br, —I, —CN, —$NO_2$, —CHO, =O, —$R^z$, —C(=O)$R^z$, —C(=O)H, —C(=O)OH, —C(=O)$OR^z$, —C(=O)$NH_2$, —C(=O)$NHR^z$, —C(=O)—N($R^z$)$_2$, —OH, —O($CH_2$)$_{1-2}$O—, —$OR^z$, —OC(=O)H, —OC(=O)$R^z$, —OC(=O)$OR^z$, —OC(=O)$NHR^z$, —OC(=O)N($R^z$)$_2$, —SH, —$SR^z$, —$SO_3H$, —S(=O)$_{1-2}$—$R^z$, —S(=O)$_{1-2}NH_2$, —$NH_2$, —$NHR^z$, —N($R^z$)$_2$, —$N^+(R^z)_3$, —$N^+(R^z)$—$_{PO(OR^z)_2}$, —NHC(=O)$R^z$, —NHC(=O)$OR^z$, —NH—C(=O)$NH_2$, —NHC(=O)$NHR^z$, —NHC(=O)-N($R^z$)$_2$, —Si($R^z$)$_3$ and —PO(O$R^z$)$_2$; wherein if necessary N-ring atoms present can be respectively oxidized.

2. The method according to claim 1, wherein $R^2$ represents —F, —Cl, —Br, —I, —O—$C_{1-8}$-alkyl, -S-phenyl, —S-$C_{1-8}$-alkyl-C(=O)NH-phenyl, —NH-$C_{1-8}$-alkyl, —NH-$C_{1-8}$-alkyl-$CO_2H$, —NH-$C_{1-8}$ -alkyl-phenyl or -$C_{3-12}$-cycloalkyl.

3. The method according to claim 2, wherein $R^2$ represents: —O—$C_{1-8}$-alkyl or —NH—$C_{1-8}$-alkyl-$CO_2H$, wherein —$C_{1-8}$-alkyl is unsubstituted.

4. The method according to claim 1, wherein $R^2$ represents —$NR^AR^B$, wherein $R^A$ and $R^B$ together with the nitrogen atom to which they are attached form a ring and mean —$(CH_2)_{2-6}$.

5. The method according to claim 2, wherein $R^2$ represents —F, —Cl, —Br, or —I.

6. The method according to claim 2, wherein $R^3$, $R^4$, $R^5$, $R^6$, $R^7$ and $R^8$ represent —H.

7. The method according to claim 3, wherein $R^3$, $R^4$, $R^5$, $R^6$, $R^7$ and $R^8$ represent —H.

8. The method according to claim 1, wherein $R^1$ and $R^2$ jointly form a five- or six-membered ring, the ring atoms of which respectively independently of one another are C, S or O, wherein the ring is aromatic or non-aromatic, unsubstituted or mono- or polysubstituted by substituents selected independently of one another from the group consisting of —C(═O)O—$C_{1-8}$-aliphatic, —C(═O)—$C_{1-8}$-aliphatic-NH-aryl, —$NH_2$, —NH—$C_{1-8}$-aliphatic and —N(—$C_{1-8}$-aliphatic)$_2$ and wherein when $R^1$ and $R^2$ form a six-membered ring, the ring comprises at least one S or O.

9. The method according to claim 8, wherein $R^1$ and $R^2$ jointly form a five-membered ring, the ring atoms of which respectively independently of one another are C or S, wherein the ring is aromatic, mono- or polysubstituted by substituents selected independently of one another from the group consisting of -C(═O)O—$C_{1-8}$-alkyl, —C(═O)—$C_{1-8}$-aliphatic-NH-phenyl and —$NH_2$.

10. The method according to claim 1, wherein the compound has the general formula (3A)

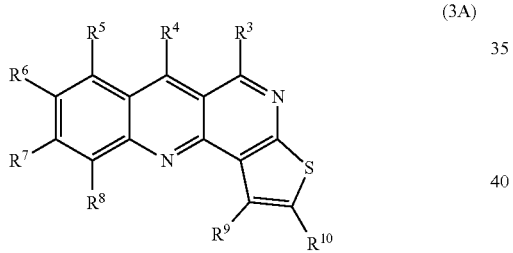

(3A)

wherein
$R^9$ represents —$NH_2$
and $R^{10}$ represents —C(═O)O—$C_{1-8}$-alkyl or —C(═O)—$CH_2$—NH—phenyl.

11. The method according to claim 1, wherein $R^3$ represents —H.

12. The method according to claim 1, wherein $R^4$ represents —H.

13. The method according to claim 1, wherein $R^5$ represents —H.

14. The method according to claim 1, wherein $R^6$ represents —H.

15. The method according to claim 1, wherein $R^7$ represents —H.

16. The method according to claim 1, wherein $R^8$ represents —H.

17. The method according to claim 1, wherein $R^3$, $R^4$, $R^5$, $R^6$, $R^7$ and $R^8$ represent —H.

18. The method according to claim 1, wherein the compound has the general formula (2)

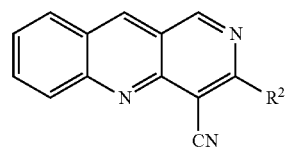

(2)

wherein
$R^2$ represents —F, —Cl, —Br, —I, —O—$C_{1-8}$-alkyl, —S—phenyl, —S—$C_{1-8}$-alkyl-C(═O)NH-phenyl, —NH—$C_{1-8}$-alkyl, —NH—$C_{1-8}$-alkyl-$CO_2$H, —NH—$C_{1-8}$-alkyl-phenyl or —$C_{3-12\text{-}cycloalkyl}$;

or having the general formula (3)

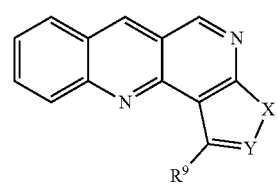

(3)

wherein
X represents —S—;
Y represents —C—$R^{10}$;
$R^9$ represents —$NH_2$; and
$R^{10}$ represents —C(═O)O—$C_{1-8}$-alkyl or —C(═O)—$C_{1-8}$-alkyl—NH—phenyl.

19. The method according to claim 18, wherein the compound has the general formula (4)

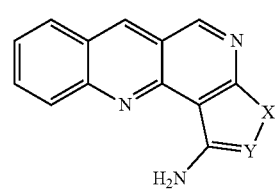

(4)

wherein
X represents —S—;
Y represents —C—$R^{10}$;
$R^{10}$ represents —C(═O)O—$C_{1-8}$-alkyl or —C(═O)—$CH_2$—NH—phenyl.

20. The method according to claim 18, wherein the compound has the general formula (2)

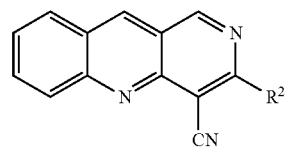

(2)

wherein
$R^2$ represents —Cl, —O—$C_{1-8}$—alkyl, —S—phenyl, —S—$C_{1-8}$-alkyl—C(═O)NH—phenyl, —NH—$C_{1-8}$-alkyl, —NH—$C_{1-8}$-alkyl-$CO_2$H, —NH—$C_{1-8}$-alkyl-phenyl or —$C_{3-12}$-cycloalkyl.

21. The method according to claim 18, wherein the compound has the general formula (2)

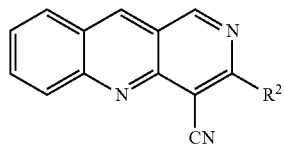
(2)

wherein

R² represents —NH—C$_{1-8}$-alkyl or —NH—C$_{1-8}$-alkyl—CO$_2$H, wherein -C$_{1-8}$-alkyl is unsubstituted.

22. The method according claim 18, wherein the compound has the general formula (2)

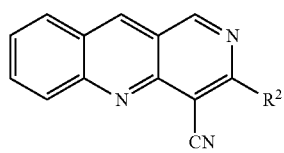
(2)

wherein

R² represents —O—C$_{1-8}$-alkyl or —NH—C$_{1-8}$-alkyl-CO$_2$H, wherein —C$_{1-8}$-alkyl is unsubstituted.

23. A method comprising:

administering to a patient in need thereof an amount of a compound effective to treat lung cancer, breast cancer, liver cancer or prostate cancer, wherein the compound is selected from the group consisting of

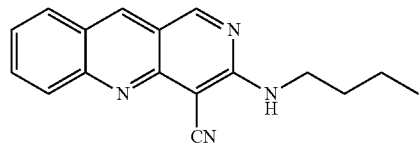
(A)

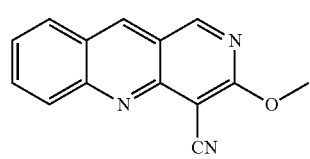
(B)

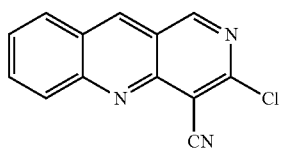
(D)

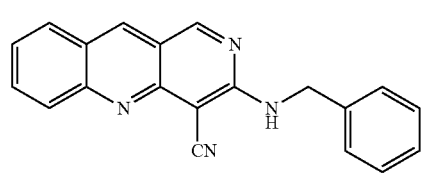
(E)

-continued

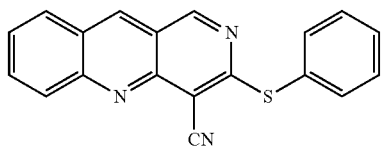
(G)

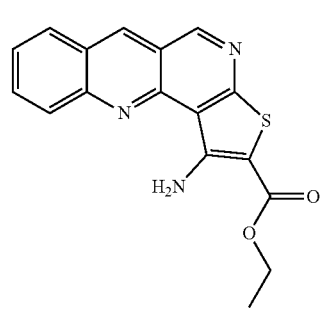
(H)

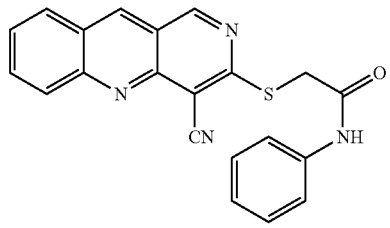
(I)

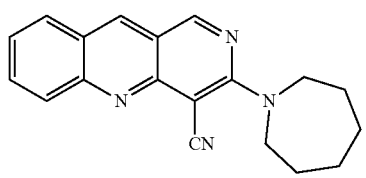
(J)

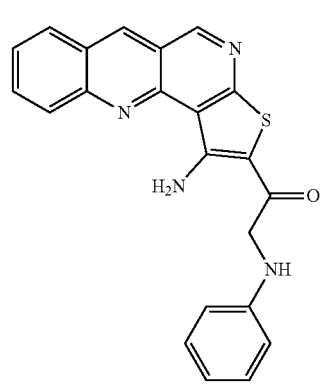
(K)

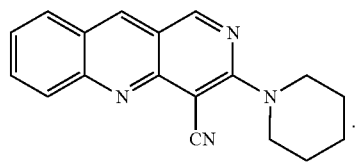
(L)

24. The method according to claim 1, wherein the compound is

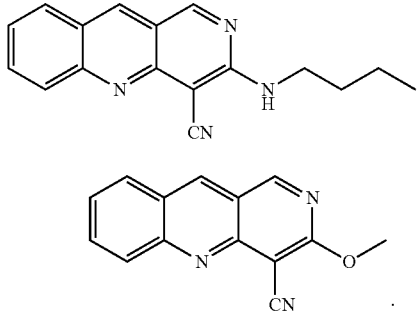

25. The method according to claim 1, wherein the compound is administered once daily, twice daily, thrice daily or more often to a subject in need thereof; and/or orally, rectally, intravenously, intramuscularly, intraperitoneally, intrasternally, subcutaneously, by intraarticular injection, by infusion, intravaginally, intracisternally, intraperitoneally, topically, bucally or extracorporeally.

26. The method according to claim 1, wherein the cancer is selected from the group consisting of tyrosine-kinase inhibitor (TKI) resistant EGFR and KRAS mutant cancers.

27. The method according to claim 1, wherein the cancer is drug resistant cancer.

28. The method according to claim 23, wherein the compound is administered to the patient in a lung cancer, breast cancer, liver cancer or prostate cancer treating effective amount.

29. The method according to claim 1, wherein the cancer is lung cancer.

30. The method according to claim 29, wherein the cancer is non-small cell lung cancer (NSCLC).

* * * * *

UNITED STATES PATENT AND TRADEMARK OFFICE
CERTIFICATE OF CORRECTION

PATENT NO. : 10,875,856 B2
APPLICATION NO. : 16/060425
DATED : December 29, 2020
INVENTOR(S) : Kamyar Hadian et al.

It is certified that error appears in the above-identified patent and that said Letters Patent is hereby corrected as shown below:

In the Specification

In Column 21, Line 40, please delete "(TM)" and insert -- (TKI) --, therefore.

In the Claims

In Column 32, Line 55, in Claim 1, please delete "—$N^+(R^z)$—$_{PO(OR^z)_2}$," and insert -- -$N^+(R^Z)_2O^-$, --, therefore.

In Column 34, Line 14, in Claim 18, please delete "—$C_{3\text{-}12\text{-}cycloalkyl}$;" and insert -- -$C_{3\text{-}12}$-cycloalkyl; --, therefore.

In Column 34, Line 31, in Claim 18, delete "$R^{1o}$" and insert -- $R^{10}$ --, therefore.

Signed and Sealed this
Nineteenth Day of April, 2022

Katherine Kelly Vidal
*Director of the United States Patent and Trademark Office*